(12) United States Patent
Ortac

(10) Patent No.: US 12,054,772 B2
(45) Date of Patent: Aug. 6, 2024

(54) METHODS FOR SINGLE MOLECULE SEQUENCING

(71) Applicant: SARMAL, INC., San Diego, CA (US)

(72) Inventor: Inanc Ortac, San Diego, CA (US)

(73) Assignee: SARMAL, INC., San Diego, CA (US)

( * ) Notice: Subject to any disclaimer, the term of this patent is extended or adjusted under 35 U.S.C. 154(b) by 820 days.

(21) Appl. No.: 16/979,804

(22) PCT Filed: Mar. 13, 2019

(86) PCT No.: PCT/US2019/022156
§ 371 (c)(1),
(2) Date: Sep. 10, 2020

(87) PCT Pub. No.: WO2019/178302
PCT Pub. Date: Sep. 19, 2019

(65) Prior Publication Data
US 2021/0040554 A1   Feb. 11, 2021

Related U.S. Application Data

(60) Provisional application No. 62/642,373, filed on Mar. 13, 2018.

(51) Int. Cl.
C12Q 1/6869 (2018.01)
C12Q 1/48 (2006.01)
C12Q 1/66 (2006.01)

(52) U.S. Cl.
CPC ........... *C12Q 1/6869* (2013.01); *C12Q 1/485* (2013.01); *C12Q 1/66* (2013.01)

(58) Field of Classification Search
CPC ........ C12Q 1/6869; C12Q 1/485; C12Q 1/66; C12Q 2527/125; C12Q 2563/107; C12Q 2563/103; C12Q 2565/301; C12N 9/0069
See application file for complete search history.

(56) References Cited

U.S. PATENT DOCUMENTS

| | | | |
|---|---|---|---|
| 6,210,891 B1 | 4/2001 | Nyren et al. | |
| 7,264,934 B2 * | 9/2007 | Fuller | C12Q 1/6869 536/23.1 |
| 9,909,177 B2 * | 3/2018 | Ju | C12Q 1/6874 |
| 2006/0051807 A1 | 3/2006 | Fuller et al. | |
| 2011/0111401 A1 * | 5/2011 | Korlach | C12Q 1/6869 435/6.12 |
| 2011/0311980 A1 * | 12/2011 | Pollack | B01L 3/502784 435/6.12 |

FOREIGN PATENT DOCUMENTS

| | | |
|---|---|---|
| JP | 2001501092 A | 1/2001 |
| WO | 2016036877 A1 | 3/2016 |
| WO | 2017014762 A1 | 1/2017 |
| WO | 2017/087823 A1 | 5/2017 |
| WO | 2018112412 A1 | 6/2018 |

OTHER PUBLICATIONS

An optimized luciferase bioluminescent assay for coenzyme A, 2008, Anal Bioanal Chem. 391:2161-2168 (Year: 2008).*
Peter A Sims et al, Fluorogenic DNA sequencing in PDMS microreactors, Nature Methods, vol. 8, No. 7, 1 January 201pp. 575-580.
International Search Report and Written Opinion for related International Application No. PCT/US2019/022156, mailed on Aug. 7, 2018 (11 pages).
Eid, J. et al. "Real-Time DNA Sequencing from Single Polymerase Molecules" Science, Jan. 2, 2009, vol. 323, Iss. 11 (25 pages).
Qiagen "Pyrosequencing—the synergy of sequencing and quantifications" Pyrosequencing Technology, 2010 (16 pages).
Leeuwen, W. et al. "The Use of the Luciferase Reporter System for in Planta Gene Expression Studies" Plant Molecular Biology Reporter, 2000 (20 pages).
Eriksson, J. et al. "Method for Real-Time Detection of Inorganic Pyrophosphatase Activity" Analytical Biochemistry, 2001, pp. 67-70; Issue 293 (4 pages).
Jonas Eriksson et al., "Method for Real-Time Detection of Inorganic Pyrophosphatase Activity", Analytical Biochemistry, vol. 293, Apr. 23, 2001; pp. 67-70.

* cited by examiner

*Primary Examiner* — Narayan K Bhat
(74) *Attorney, Agent, or Firm* — PROCOPIO, CORY, HARGREAVES & SAVITCH LLP

(57) ABSTRACT

Provided herein are methods and systems for sequencing a single nucleic acid molecule utilizing a polymerase enzyme, a template nucleic acid, and a polymerase reagent solution, including components for a luminescence reaction.

20 Claims, 14 Drawing Sheets

Specification includes a Sequence Listing.

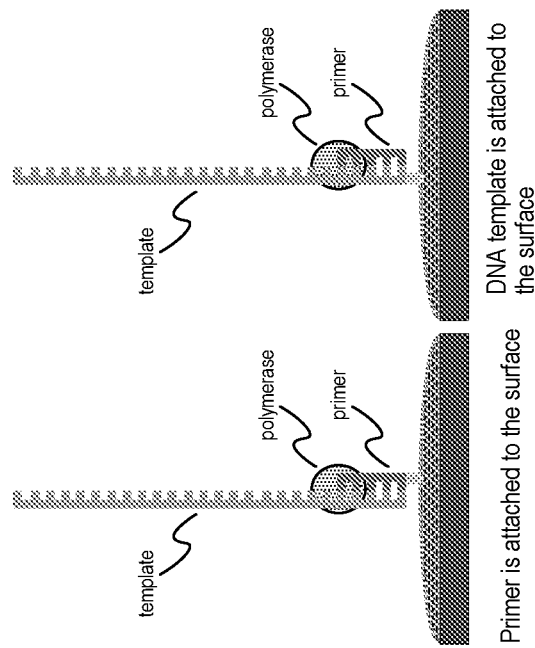

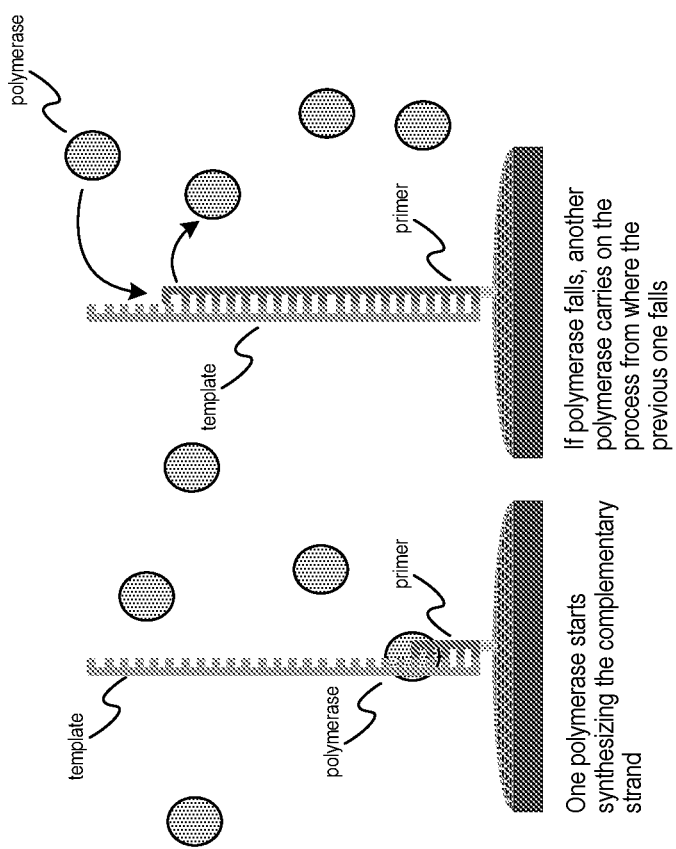

SEQUENCE LISTING

<160> NUMBER OF SEQ ID NOS: 2

<210> SEQ ID NO 1
<211> LENGTH: 111
<212> TYPE: DNA
<213> ORGANISM: Artificial Sequence
<220> FEATURE:
<223> OTHER INFORMATION: Template DNA

<400> SEQUENCE: 1
cccccccccc cccccccccc cccccccccc cccccccccc cccccccccc cccccccccc    60
cccccccccc cccccccccc cccccccccc aaatcttatc atcggtcggt g             111

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
caccgaccga tgataagatt t                                               21

METHODS FOR SINGLE MOLECULE SEQUENCING

CROSS-REFERENCE TO RELATED APPLICATIONS

This application is a U.S. National Stage entry of PCT Application No: PCT/US2019/022156 filed Mar. 13, 2019, which claims priority to U.S. Provisional Patent Application No. 62/642,373, filed Mar. 13, 2018, the contents of which are incorporated herein by reference.

TECHNICAL FIELD

The invention relates to methods for single molecule nucleic acid sequencing.

INTRODUCTION

Current sequencing technologies can be grouped into two main categories: short-read sequencing and long-read sequencing. In each category, DNA is cleaved into pieces with lengths up to a certain number of nucleotides or basepairs (bp). In all cases, all pieces of DNA are spread into a 2 dimensional array and are detected by a sensor array corresponding to where at least one sensor is matched with a piece of DNA.

Short-read sequencing approaches are simple cycle based technologies that includes sequencing-by-ligation (SBL) and sequencing-by-synthesis (SBS). SBL approaches includes SOLID (Thermo Fisher) and Complete Genomics (BGI). With SOLID, read lengths around 75 basepairs (bps) is reached while with Complete Genomics approach 28 to 100 basepair reads are feasible. With these approaches structural variation and genome assembly is not possible and they are susceptible to homopolymer errors. Their runtimes are on the order of several days. Illumina and Qiagen's GeneReader technology use SBS approach with Cyclic Reversible Termination. They can reach up to 300 bp. However, a major drawback is under representation of AT and GC rich regions, substation errors and high half positive rate. On the other hand, other SBS approaches such as 454 pyrosequencing and Ion Torrent (Thermo Fisher) use single-nucleotide Addition/Termination. 454 pyrosequencing could reach 400 bp while Ion Torrent can achieve 700 bp read lengths. However, although these technologies are faster and good for point of care, they also have many drawbacks including domination of insertion/deletion errors, and homopolymer region errors. They cannot be used to reveal long-range genomic or transcriptomic structure, and cannot do paired end sequencing.

Long-read sequencing approaches include two main types, synthetic long-read sequencing or real-time long-read sequencing. Synthetic pieced together long-read sequencing used by Illumina and 10x Genomics focuses on library preparation that leverages barcodes and allows computational assembly of large fragments. In fact, these technologies do not do actual long-reads, rather they do short-reads, in which the DNA pieces are organized using a barcoding approach, which helps eliminate some complexity during analysis, which allows obtaining data similar to actual long-read methods. However, this approach has a very high cost due, in part, to its requiring even more coverage. The other type of long-read sequencing is real-time long-read sequencing, which has been used by Pacific Biosciences and Oxford Nanopore Technologies. Unlike synthetic long-read sequencing, real-time long-read sequencing does not rely on clonal population of amplified DNA and does not require chemical cycling. Nanopore's technology has very high error rates around 30%, which also require very high coverage that contributes significantly to the cost. Using modified bases has also been particularly challenging for Nanopore's technology, which has generated unique signals that makes the analysis even more complex. Pacific Biosciences can reach read lengths up to 4000-5000 bps. However, due to high single-pass error rates around 15% for long reads, high coverage is required, which makes 1 Gb sequencing cost more than $1000 (see, e.g., Goodwin et al., Nat. Rev. Genet. 17:333-351; 2016). In addition, the thermal background present and excitation energy utilized by these methods damages the DNA polymerases used in the critical reactions, which ultimately limits the read lengths and applicability of this technology. In addition, as the luminescence generated is a generic spectrum independent of the nucleotide attached by the polymerase, pyrosequencing requires a cycle-based approach where each nucleotide is administered one by one collecting signal from all the binding events. This is followed with a washing cycle to remove the unbound nucleotides to administer the next nucleotide.

Since, a large majority of current technologies offer short read lengths (around 40-100 bases long) of nucleotides per unit, one of the most challenging problem lies in alignment of small pieces of sequences into one large meaningful sequence, and analyzing high coverage data and the post-processing of the loads of generated data with complicated algorithms using powerful super computers. Newer generation single molecule based sequencing technologies can potentially address this issue. However, each of these prior art technologies have high error rates requiring high coverages (multiple reads of the same region of a sequence) often around 30× to 100× in order to obtain a reliable data.

Accordingly, there is a need for improved methods for single molecule nucleic acid sequencing.

SUMMARY

Provided herein are methods for sequencing a nucleic acid template comprising:

providing a sequencing mixture comprising (i) a polymerase enzyme, (ii) an ATP regenerating enzyme, (iii) a luminescence enzyme (e.g., firefly luciferase), (iv) a template nucleic acid, and (iii) a polymerase-ATP regenerating enzyme-luminescence reagent solution having the components for carrying out template directed synthesis of a growing nucleic acid strand, wherein said reagent solution includes an ATP-regenerating-enzyme-substrate (e.g., APS, ADP-glucose, AMP+PEP, and the like), a luminescence-substrate (e.g., luciferin); and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand;

carrying out nucleic acid synthesis such that a plurality of nucleotide analogs are added sequentially to the template whereby: a) a nucleotide analog associates with the polymerase, b) the nucleotide analog is incorporated on the template strand by the polymerase when the labeled leaving group on that nucleotide analog is cleaved by the polymerase, wherein the labeled leaving group is combined with an ATP-regenerating-enzyme-substrate by the ATP regenerating enzyme (e.g., with APS by ATP Sulfurylase; with ADP-glucose by AGPPase; with AMP+PEP by PPDK, and the like) yielding labeled-ATP, then c) binding the labeled-ATP to a luminescence-enzyme (firefly luciferase), wherein a luminescence-substrate (luciferin) is catalyzed by the luminescence-enzyme (luciferase) to produce luminescence for a limited (transient/discreet) period of time and regenerate the respective labeled leaving group, wherein said luminescence causes (excites) the label on the respective labeled leaving group to produce light; and detecting light from the labels while nucleic acid synthesis is occurring, and using light detected during each discreet luminescence period (event), to determine a sequence of the template nucleic acid.

A key advantage of the invention sequencing methods (also referred to herein as the FLASH sequencing method) is that the polymerase enzyme is not damaged in the invention reaction conditions, such as by being attached to a particular surface, or being subject to multiple exposures to external light excitation used to generate signal; as occurs with existing methods. In the invention methods, the polymerase is not modified, attached, exposed to external light sources, or otherwise pressured away from performing its native chain elongation function. This advantageously results in a longer functioning polymerase able to reach very long read lengths with as much accuracy high fidelity as occurs in its native environment, with much less coverage than existing methods.

For example, in particular embodiments of the present invention, either a single polymerase or a plurality of polymerases are confined with the sequencing reaction mixture in a single droplet, wherein the polymerase(s) is not subject to external light excitation to generate the dNTP incorporation signal to be detected.

In a particular embodiment, the sequencing mixture further comprises a pyrophosphatase enzyme capable of converting the labeled pyrophosphate into 2 phosphate ions. The ratios of enzyme concentrations are adjusted such that ATP sulfurylase/Luciferase loop activity is orders of magnitude higher than the pyrophosphatase activity. In one embodiment, the relative reaction rate of ATP-Sulfurylase/Luciferase loop is in the range of $10^3$-$10^{12}$ times faster than the pyrophosphatase reaction. In another embodiment, the luciferase and pyrophosphatase are co-encapsulated in a nanomatrix. In one embodiment, the nanomatrix is a nanoparticle that is negatively charged. In this embodiment, labeled ATP (ATP-FL) is able to diffuse into the negatively charged matrix in which luciferase and pyrophosphatase are co-encapsulated. In a particular embodiment, the step c) binding the labeled-ATP to a luminescence-enzyme, wherein a luminescence-substrate is catalyzed by the luminescence-enzyme, occurs within the nanomatrix.

The invention methods are useful for a variety of uses including whole genome sequencing, SNP-variant detection, and the like. One advantage of the invention methods over existing methods is the utilization of ATP labeled with a fluorophore (e.g., labeled-ATP) in a luminescence reaction, for example using firefly luciferase and luciferin to generate a controlled, uniquely defined, discreet and/or transient limited luminescence period that excites the fluorophore label. It has surprisingly been found that such labeled-ATP could function in a luminescence reaction using firefly luciferase and luciferin. Another advantage of the invention methods over existing methods is the reduction in light intensity utilized by the luminescence reaction for exciting a fluorophore label, such that damage to the DNA polymerase does not occur. For example, the luminescence light intensity can be reduced compared to existing sequencing methods by at least 5-fold, 10-fold, 25-fold, 50-fold, 75-fold, 100-fold up to at least 1,000-fold. In particular embodiments, the reduction in light intensity utilized to excite the labels (e.g., fluorophore) utilized herein, can be at least 5-fold, 10-fold, 25-fold, 50-fold, 75-fold, 100-fold, 200-fold, 300-fold, 400-fold, 500-fold, 600-fold, 700-fold, 800-fold, 900-fold, 1000-fold, 2000-fold, and the like. This advantage results in the longer functioning of the DNA polymerase, thereby producing longer read lengths.

The disclosed invention is a single molecule sequencing technology based on monitoring individual polymerase enzymes as they incorporate dNTPs sequentially. In a particular embodiment, the invention encompasses a process where each time polymerase incorporates a dNTP complementary to the template, a fluorescence signal is transiently, uniquely and/or discreetly generated during the incorporation process, wherein such fluorescence is caused by excitation from a transient, unique and/or discreet luminescence reaction. In other words, the luminescence reaction causes a labeled leaving group (e.g., a labeled pyrophosphate), via the excitation spectra and the like, to emit a detectable light signal for a limited amount of time specific for that particular dNTP. The process repeats for the next dNTP incorporation (FIG. 1).

More particularly, each time a polymerase incorporates a modified deoxyribonucleoside triphosphate (dNTP) nucleotide analog to the strand complementary to the template DNA, a fluorescence signal specific to the type of the nucleotide attached is generated. There are four types of dNTPs, namely deoxyadenosine triphosphate (dATP), deoxyguanosine triphosphate (dGTP), deoxycytidine triphosphate (dCTP), and deoxythymidine triphosphate (dTTP). Each nucleotide generates a unique fluorescence signal (e.g., in red, yellow, green, or blue, and the like) while they are being attached to the complementary strand by the polymerase enzyme. Upon the completion of attachment of the nucleotide analog to the 3' moiety of the previously attached nucleotide analog, the fluorescence generated by the leaving group is detected by an appropriate fluorescence sensor and/or detection device and then, in some embodiments, it is subsequently rapidly terminated by decay of luminescence reaction for that respective dNTP incorporation. In other words, each dNTP incorporated into the template strand results in a discreet, limited-period pulse of light (fluorescence signal) that is unique and indicative of that respective dNTP incorporation event.

In other embodiments, the fluorescence generated by the leaving group is amplified by and detected by an appropriate fluorescence sensor and/or detection device and then, in some embodiments, it is subsequently rapidly terminated by decay of luminescence reaction for that respective dNTP incorporation.

Also provided herein is a method of amplifying a detectable light signal from an ATP regenerating enzyme/luciferase loop, said method Sequencing is achieved by detecting the fluorescence generated each time a nucleotide is added to the complementary strand revealing the type of nucleotide. Therefore, each specific nucleotide attachment generates a short peak of a fluorescence signal that can be detected by a fluorescence sensor. As a result, a data array of succeeding, sequential colors is produced, which can be converted into a corresponding data array of nucleotide sequence (FIG. 1).

An advantage provided by the invention methods disclosed herein lies in its simplicity and innovative chemistry that significantly reduces background signal during detection thereby improving sensitivity. In accordance with the present invention methods, less modification of the reaction conditions involving reagents and enzymes improves specificity, efficiency and rate. Also, in accordance with the present invention methods, polymerase operates in near ideal conditions, and is contemplated to reach very long read lengths around tens of thousands of bases per DNA polymerase molecule by utilizing high sensitivity and specificity together with requiring significantly less post-processing and analysis of the data produced. The combined features of the invention methods disclosed herein reduces the cost both for the respective devices and each run, while achieving high specificity in addition to decreasing the time per test considerably compared to competing technologies. Accordingly, the disclosed invention methods and systems allow realization of very low cost and real-time sequencing systems without adversely affecting specificity.

INCORPORATION BY REFERENCE

Herein, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

FIG. 10A shows the configuration where the primer is attached to a solid surface substrate, for subsequent biding of the target template nucleic acid.

FIG. 10B shows the configuration where the target nucleic acid template is attached to a solid surface substrate, for subsequent biding of the primer.

FIG. 11A shows an embodiment of initiating the invention sequencing methods using a plurality of polymerases on a single target nucleic acid template.

FIG. 11B shows an embodiment where the sequencing of the target template is substantially continuous because as the polymerase that starts synthesizing the complementary strand traverses its typical read length, then falls off or dissociates from template, another of the many other polymerases in the reaction mixture immediately binds to the template and continues the complementary strand sequencing synthesis.

DETAILED DESCRIPTION

Figure 1:
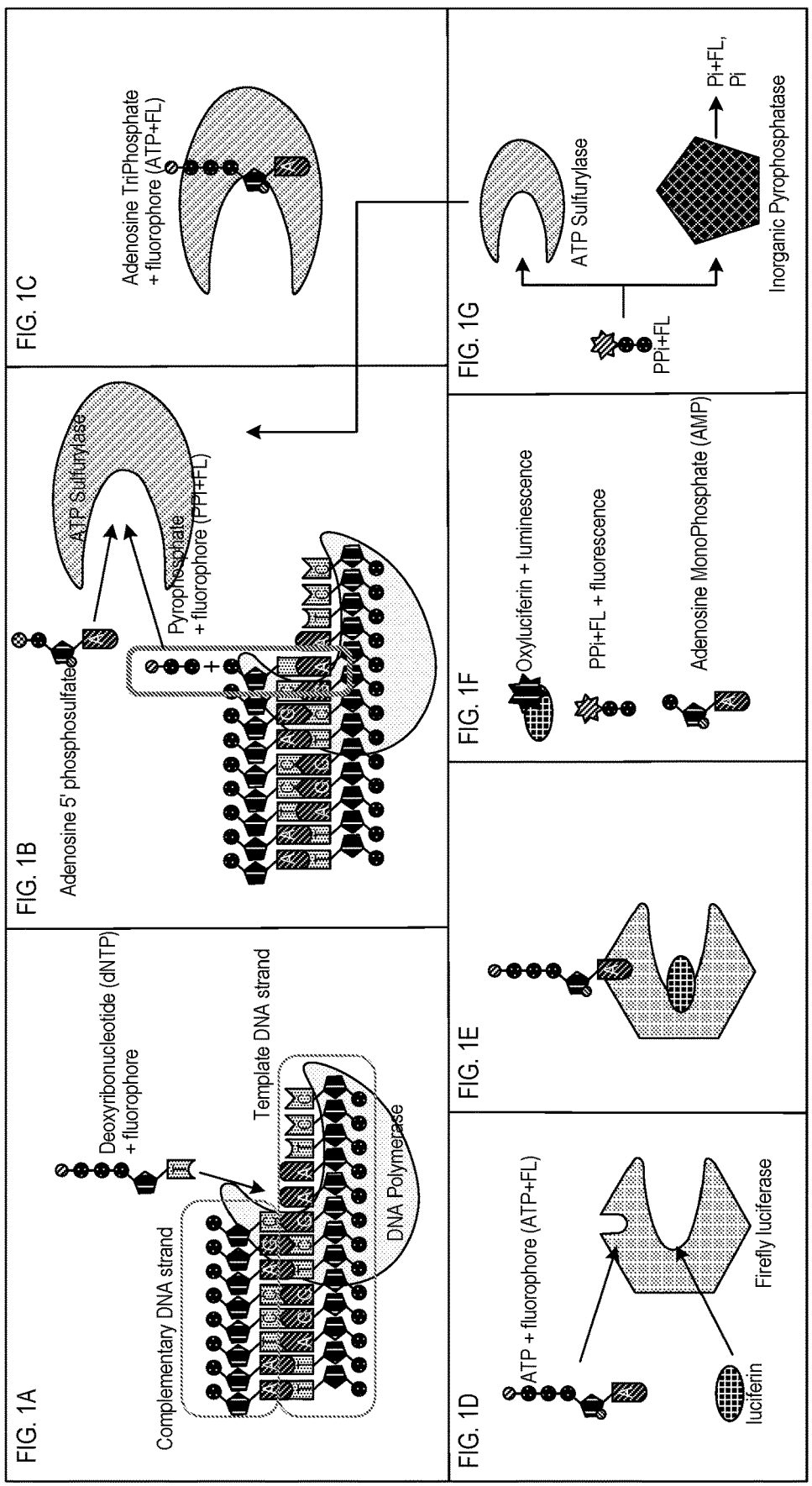
FIG. 1A shows a general illustration of one embodiment of the invention sequencing method: DNA Polymerase uses modified dNTPs with respective fluorophore levels as building blocks. Upon binding to polymerase, the pyrophosphate containing a fluorescent molecule is cleaved off for later reactions.
FIG. 1B shows the polymerase-dependent binding of a respective nucleotide analog having a fluorophore attached therein to the template strand and the cleaving of the labeled pyrophosphate that has the fluorophore attached, which will next interact with ATP sulfurylase, which binds the respective labeled pyrophosphate to adenosine 5'-phosphosulfate (APS), resulting in a labeled ATP (ATP+FL).
FIG. 1C shows the formation of labeled ATP.
FIG. 1D shows the reagents, labeled-ATP (ATP+FL), luciferin, and firefly luciferase, for the luminescence reaction set forth herein.
FIG. 1E shows the interaction of the reagents in the luminescence reaction, from which the labeled pyrophosphate will fluoresce as a result of the concomitant luminescence.
FIG. 1F further shows that during the nucleotide analog dNTP interaction with polymerase, fluorescence is generated upon cleavage of the labeled pyrophosphate from the labeled-ATP, generating a fluorescence signal corresponding to the color of the respective fluorophore. There is a unique colored fluorophore for each class of nucleotide analog dNTPs, such that each type of nucleotide analog has a different label (e.g., a different FL).
FIG. 1G shows the luminescence generation as a result of the polymerase-ATP sulfurylase-luciferase reaction (also referred to as FLASH reaction) by varying either the ATP Sulfurylase, Firefly luciferase, or dGTP-Coumarin amounts as set forth in Example 2.

Provided herein are methods for sequencing a nucleic acid template, wherein said methods comprise:

providing a sequencing mixture comprising (i) a polymerase enzyme, (ii) an ATP regenerating enzyme, (iii) a luminescence enzyme (e.g., firefly luciferase), (iv) a template nucleic acid, and (iii) a polymerase-ATP regenerating enzyme-luminescence reagent solution having the components for carrying out template directed synthesis of a growing nucleic acid strand, wherein said reagent solution includes an ATP-regenerating-enzyme-substrate (e.g., APS, ADP-glucose, AMP+PEP, and the like), a luminescence-substrate (e.g., luciferin); and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand;

carrying out nucleic acid synthesis such that a plurality of nucleotide analogs are added sequentially to the template whereby: a) a nucleotide analog associates with the polymerase, b) the nucleotide analog is incorporated on the template strand by the polymerase when the labeled leaving group on that nucleotide analog is cleaved by the polymerase, wherein the labeled leaving group is combined with an ATP-regenerating-enzyme-substrate by the ATP regenerating enzyme (e.g., with APS by ATP Sulfurylase; with ADP-glucose by AGPPase; with AMP+PEP by PPDK, and the like) yielding labeled-ATP, then c) binding the labeled-ATP to a luminescence-enzyme (firefly luciferase), wherein a luminescence-substrate (luciferin) is catalyzed by the luminescence-enzyme (luciferase) to produce luminescence for a limited (transient/discreet) period of time and regenerate the respective labeled leaving group, wherein said luminescence causes (excites) the label on the respective labeled leaving group to produce light; and detecting light from the labels while nucleic acid synthesis is occurring, and using light detected during each discreet luminescence period (event), to determine a sequence of the template nucleic acid.

In particular embodiments of the invention methods said methods comprise:

providing a sequencing mixture comprising (i) a polymerase enzyme, (ii) an ATP sulfurylase, (iii) a luminescence enzyme (e.g., firefly luciferase), (iv) a template nucleic acid, and (iii) a polymerase-sulfurylase-luminescence reagent solution having the components for carrying out template directed synthesis of a growing nucleic acid strand, wherein said reagent solution includes APS, a luminescence-substrate (e.g., luciferin); and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand; or providing a sequencing mixture comprising (i) a polymerase enzyme, (ii) an ADPglc pyrophosphorylase (AGPPase), (iii) a luminescence enzyme (e.g., firefly luciferase), (iv) a template nucleic acid, and (iii) a polymerase-AGPPase-luminescence reagent solution having the components for carrying out template directed synthesis of a growing nucleic acid strand, wherein said reagent solution includes ADP-glucose, a luminescence-substrate (e.g., luciferin); and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand; or providing a sequencing mixture comprising (i) a polymerase enzyme, (ii) a pyruvate orthophosphate dikinase (PPDK), (iii) a luminescence enzyme (e.g., firefly luciferase), (iv) a template nucleic acid, and (iii) a polymerase-PPDK-luminescence reagent solution having the components for carrying out template directed synthesis of a growing nucleic acid strand, wherein said reagent solution includes AMP and phosphoenalpyruvate (PEP), a luminescence-substrate (e.g., luciferin); and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand; and carrying out nucleic acid synthesis such that a plurality of nucleotide analogs are added sequentially to the template whereby: a) a nucleotide analog associates with the polymerase, b) the nucleotide analog is incorporated on the template strand by the polymerase when the labeled leaving group on that nucleotide analog is cleaved by the polymerase, wherein the labeled leaving group is combined with either: APS by ATP Sulfurylase, ADP-glucose by AGGPase; and/or AMP by PPDK, yielding labeled-ATP, then c) binding the labeled-ATP to a luminescence-enzyme (firefly luciferase), wherein a luminescence-substrate (luciferin) is catalyzed by the luminescence-enzyme (luciferase) to produce luminescence for a limited (transient/discreet) period of time and regenerate the respective labeled leaving group, wherein said luminescence causes (excites) the label on the respective labeled leaving group to produce light; and detecting light from the labels while nucleic acid synthesis is occurring, and using light detected during each discreet luminescence period (event), to determine a sequence of the template nucleic acid.

As used herein, "polymerase-ATP regenerating enzyme-luciferase" or grammatical variations thereof, refers to any concatenated 3 Enzyme System known in the art that can be used in the invention methods to utilize the labeled pyrophosphate generated by the polymerase chain elongation sequencing reaction, and convert the labeled pyrophosphate (PPi; FIG. 1B) into ATP. For example, a concatenated 3 Enzyme polymerase-ATP regenerating enzyme-luciferase system can be selected from the group consisting of: a polymerase-ATP sulfurylase-luminescence enzyme system; a polymerase-AGPPase-luminescence (as disclosed in Lee et al., Analytical Biochemistry, 399 (2010) 168-173; incorporated herein by reference in its entirety for all purposes); a polymerase-PPDK-luminescence enzyme system (as disclosed in Zhou et al., Anal. Chem. 2006, 78, 4482-4489; incorporated herein by reference in its entirety for all purposes); and the like.

As used herein, the phrase "ATP-regenerating-enzyme-substrate" refers to the native substrate for a respective ATP-regenerating enzyme used herein. For example, the native substrate used herein for ATP sulfurylase is APS; for AGGPase is ADP-glucose; for PPDK is AMP+PEP, and the like.

As use herein, the term "ATP regenerating enzyme/ Luciferase loop" or "ATP regenerating enzyme/Luciferase signal amplification loop" grammatical variations thereof (e.g., ATP Sulfurylase/Luciferase loop, AGPPase/Luciferase loop, PPDK/luciferase loop, and the like), refers generally to an enzymatic loop between the ATP regenerating enzyme and luciferase as set forth in Example 3 herein and in FIG. 1B-1G, whereby following the luminescent reaction catalyzed by luciferase a new pyrophosphate molecule is released still having the fluorescent label attached (PPi+FL) (FIG. 1F). This newly released PPi-FL can once again be a substrate for the ATP regenerating enzyme (e.g., ATP Sulfurylase, AGPPase, PPDK, and the like) thereby generating an enzymatic loop between ATP regenerating enzyme (e.g., ATP Sulfurylase, AGPPase, PPDK, and the like) and luciferase (FIG. 1G.Top). As shown in FIG. 1B-1G, within this loop PPi+FL is recycled by ATP Sulfurylase and converted into fluorescently labeled ATP (ATP-FL), which can then be catalyzed by luciferase releasing PPi-FL. This will generate successive signals from the labeled pyrophosphate, and thereby serve as an amplification mechanism for the sequencing signal for the most recent nucleotide.

In a particular embodiment, the sequencing mixture further comprises a pyrophosphatase enzyme capable of converting the labeled pyrophosphate into 2 phosphate ions, which functions in the invention methods to break the "ATP regenerating enzyme/Luciferase signal amplification loop" prior to the incorporation of the next dNTP in the chain elongation sequencing reaction. Exemplary concatenate polymerase-ATP regenerating enzyme-luciferase-pyrophosphatase 4 Enzyme systems for use herein include: polymerase-ATPsulfurylase-luciferase-pyrophosphatase; polymerase-AGPPase-luciferase-pyrophosphatase; and polymerase-PPDK-luciferase-pyrophosphatase, and the like. In this embodiment, the ratios of enzyme concentrations are adjusted such that ATP regenerating enzyme/Luciferase loop activity is orders of magnitude higher than the pyrophosphatase activity. In one embodiment where the concatenate polymerase-ATP regenerating enzyme-luciferase-pyrophosphatase 4 Enzyme system is used, the relative reaction rate of ATP regenerating enzyme/Luciferase loop is selected to be in the range $10^3$-$10^{12}$, $10^3$-$10^{10}$, $10^3$-$10^9$, $10^3$-$10^8$, $10^3$-$10^7$, and $10^3$-$10^6$, and the like, times faster than the pyrophosphatase reaction. In other embodiments, the relative reaction rate of ATP regenerating enzyme/Luciferase loop is selected from the group consisting of at least: to $10^2$, $10^3$, $10^4$, $10^5$, $10^6$, $10^7$, $10^8$, $10^9$, $10^{10}$, $10^{11}$, $10^{12}$, and the like, times faster than the pyrophosphatase reaction.

In other embodiments, to control the rate of the ATP regenerating enzyme/Luciferase loop reaction relative the rate of the pyrophosphatase reaction in the invention sequencing methods; or the overall length of time of the ATP regenerating enzyme/Luciferase loop reaction, the ratio of the ATP regenerating enzyme to the pyrophosphatase enzyme can be modified and adjusted. Accordingly, provided herein are methods of modulating the length of time of the signal of an ATP regenerating enzyme/luciferase amplification loop in a sequencing reaction, comprising conducting the FLASH sequencing methods described herein; and adding pyrophosphatase to the sequencing mixture, in a ratio of pyrophosphatase to ATP regenerating enzyme effective to modulate the length of time of a signal of an ATP regenerating enzyme/luciferase amplification loop.

Depending on which ATP regenerating enzyme is selected for use herein, exemplary ATP regenerating enzyme:pyrophosphatase enzyme ratios contemplated for use herein, effective to modulate the length of time of a signal of an ATP regenerating enzyme/luciferase amplification loop, can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 ATP regenerating enzyme:pyrophosphatase enzyme, and the like. Likewise, depending on which ATP regenerating enzyme is selected for use herein, exemplary pyrophosphatase:ATP regenerating enzyme ratios contemplated for use herein, can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 pyrophosphatase:ATP regenerating enzyme, and the like.

In a particular embodiment where ATP sulfurylase and APS are used in the invention sequencing methods, exemplary ATP sulfurylase enzyme: pyrophosphatase enzyme ratios contemplated for use herein, are selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 ATP sulfurylase enzyme:pyrophosphatase enzyme, and the like.

In another embodiment, the sequencing mixture further comprises an apyrase enzyme capable of degrading dNTPs to AMP, which functions in the invention methods to break the "ATP regenerating enzyme/Luciferase signal amplification loop" prior to the incorporation of the next dNTP in the chain elongation sequencing reaction. Exemplary concatenate polymerase-ATP regenerating enzyme-luciferase-pyrophosphatase 4 Enzyme systems for use herein include: polymerase-ATPsulfurylase-luciferase-apyrase; polymerase-AGPPase-luciferase-apyrase; and polymerase-PPDK-luciferase-apyrase, and the like. In this embodiment, the ratios of enzyme concentrations are adjusted such that ATP regenerating enzyme/Luciferase loop activity is orders of magnitude higher than the apyrase activity. In one embodiment where the concatenate polymerase-ATP regenerating enzyme-luciferase-pyrophosphatase 4 Enzyme system is used, the relative reaction rate of ATP regenerating enzyme/Luciferase loop is selected to be in the range $10^3$-$10^{12}$, $10^3$-$10^{11}$, $10^3$-$10^{10}$, $10^3$-$10^9$, $10^3$-$10^8$, $10^3$-$10^7$, and $10^3$-$10^6$, and the like, times faster than the apyrase reaction. In other embodiments, the relative reaction rate of ATP regenerating enzyme/Luciferase loop is selected from the group consisting of at least: to $10^2$, $10^3$, $10^4$, $10^5$, $10^6$, $10^7$, $10^8$, $10^9$, $10^{10}$, $10^{11}$, $10^{12}$, and the like, times faster than the apyrase reaction.

In other embodiments, to control the rate of the ATP regenerating enzyme/Luciferase loop reaction relative the rate of the apyrase reaction in the invention sequencing methods; or the overall length of time of the ATP regenerating enzyme/Luciferase loop reaction, the ratio of the ATP regenerating enzyme to the apyrase enzyme can be modified and adjusted. Depending on which ATP regenerating enzyme is selected for use herein, exemplary ATP regenerating enzyme:apyrase enzyme ratios contemplated for use herein, can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 ATP regenerating enzyme: apyrase enzyme, and the like. Likewise, depending on which ATP regenerating enzyme is selected for use herein, exemplary apyrase:ATP regenerating enzyme ratios contemplated for use herein, can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 apyrase:ATP regenerating enzyme, and the like.

Figure 5:
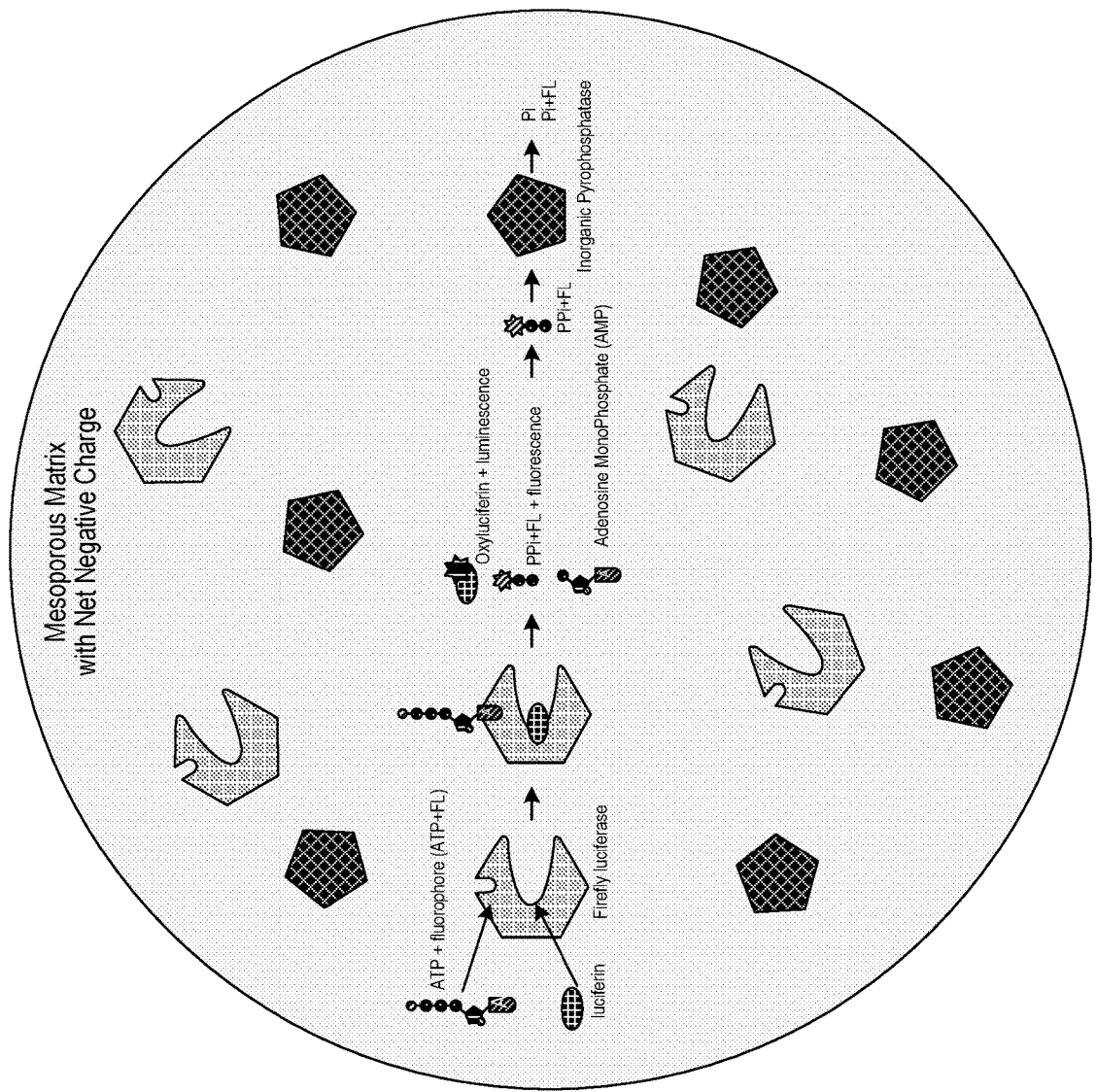
FIG. 5 shows a Mesoporous Matrix with a Net Positive Charge for co-encapsulating luciferase and pyrophosphatase as described in Example 4.

In another embodiment of the invention methods, the luciferase and pyrophosphatase are co-encapsulated in a nanomatrix. In one embodiment, the nanomatrix is a nanoparticle that is negatively charged, as set forth in FIG. 5. In this embodiment, labeled ATP (ATP-FL) is able to diffuse into the negatively charged matrix in which luciferase and pyrophosphatase are co-encapsulated. In a particular embodiment, the step c) binding the labeled-ATP to a luminescence-enzyme, wherein a luminescence-substrate is catalyzed by the luminescence-enzyme, occurs within the nanomatrix.

As used herein, the phrase "sequencing mixture" refers to the components that are used to carry out the invention single molecule sequencing reactions. In one embodiment, the sequencing mixture includes (i) a polymerase enzyme, (ii) an ATP regenerating enzyme (e.g., ATP Sulfurylase, AGPPase, PPDK, and the like), (iii) a luminescence enzyme (e.g., firefly luciferase), (iv) a template nucleic acid, and (iii) a polymerase-ATP regenerating enzyme-luminescence reagent solution having the components for carrying out template directed synthesis of a growing nucleic acid strand, wherein said reagent solution includes either APS, ADP-glucose, AMP+PEP, or the like, a luminescence-substrate (e.g., luciferin); and a plurality of types of labeled nucleotide analogs therein. In accordance with the present invention, the sequencing mixture used provides the following advantages in the invention sequencing methods over previous sequencing methods: the polymerase employed functions in its ideal state; there is no need to modify a polymerase enzyme; the use of high nucleotide (e.g., dNTP) concentrations results in optimum efficiency; requires only very-low intensity, discreet and limited period excitation light via the luminescence reaction, which advantageously reduces photobleaching of the fluorophores and reduces the denaturing of the polymerase enzyme; provides virtually no fluorescent background, which improves specificity and sensitivity of the base calling; does not require sophisticated optics or nanostructured chip design, which reduces cost; it provides high specificity, which reduces the need for high coverage; and provides long read lengths (e.g., about 50 Kb to 1 gene/cell) with much less computer processing required relative to prior art methods.

As used herein, the phrase "polymerase-ATP regenerating enzyme-luminescence reagent solution," grammatical variations thereof using either of ATP Sulfurylase, AGPPase, PPDK, and the like as the ATP regenerating enzyme, or "reagent solution" refers to the mixture of components necessary for carrying out the template directed synthesis of a growing nucleic acid. In one embodiment using ATP sulferylase, the polymerase reagent solution for use with a polymerase, e.g., DNA pol I, ATP sulfurylase, and the luminescence-enzyme (e.g., luciferase, and the like), includes a APS (adenosine 5' phosphosulfate), luciferin and suitable concentrations of dNTPs, e.g., fluorophore-modified nucleotide analogs described herein. In another embodiment using AGPPase, the polymerase reagent solution for use with a polymerase, e.g., DNA pol I, AGPPase, and the luminescence-enzyme (e.g., luciferase, and the like), includes a ADP-glucose, luciferin and suitable concentrations of dNTPs, e.g., fluorophore-modified nucleotide analogs described herein. In another embodiment using PPDK, the polymerase reagent solution for use with a polymerase, e.g., DNA pol I, PPDK, and the luminescence-enzyme (e.g., luciferase, and the like), includes a AMP+PEP, luciferin and suitable concentrations of dNTPs, e.g., fluorophore-modified nucleotide analogs described herein. In a particular embodiment, the concentrations of dNTPs employed are much higher than has been heretofore possible because, in part, of the low fluorescent background resulting from the labeled leaving groups (e.g., fluorescent pyrophosphate; PP) advantageously employed in the invention methods. Because the labeled-ATP forming enzyme (e.g., ATP Sulfurylase, AGPPase, PPDK, and the like) and polymerase rates can vary significantly depending on the type and source of the enzymes, the rate of labeled-ATP formation achieved by the ATP regenerating enzyme (e.g., ATP Sulfurylase, AGPPase, PPDK, and the like) reaction employed herein can be adjusted separately by adjusting reaction conditions such as ATP regenerating enzyme concentration, and the like as described herein.

As used herein the phrase "labeled-ATP reaction" refers to any reaction that can combine a pyrophosphate labeled with a fluorophore (PPi+FL) with an ATP regenerating substrate (e.g., either Adenosine 5' phosphosulfate (APS), ADP-glucose, AMP+PEP, or the like) to form a labeled-ATP (ATP+FL), as set forth in FIGS. 1B and 1C. In one embodiment for use herein, a labeled pyrophosphate can be combined with APS using the ATP sulfurylase enzyme, or the like. In another embodiment for use herein, a labeled pyrophosphate can be combined with ADP-glucose using the AGPPase enzyme, or the like. In another embodiment for use herein, a labeled pyrophosphate can be combined with AMP+PEP using the PPDK enzyme, or the like.

As used herein the phrase "luminsescence reaction" refers to any reaction that can produce the emission of light that does not derive at all or solely derives energy from the temperature of the emitting body (i.e., emission of light other than incandescent light). "Luminescence" includes, but is not limited to, fluorescence, phosphorescence, thermoluminescence, chemiluminescence, electroluminescence and bioluminescence. "Luminescent" refers to an object that exhibits luminescence. In preferred embodiments, the light is in the visible spectrum. However, the present invention is not limited to visible light, but includes electromagnetic radiation of any frequency. In one embodiment, the luminescence reaction employed herein is caused by the luminescence enzyme, luciferase (e.g., firefly luciferase) catalyzing the luminescence-substrate, luciferin, using the labeled-ATP (ATP+FL) as a cofactor to produce luminescence, oxylucferin, AMP and also to regenerate the labeled pyrophosphate (PPi+FL)(see FIGS. 1D-1F).

For example, in one embodiment, the iterative sequencing cycle contemplated herein involves a first labeled-ATP reaction of PPi with APS, catalyzed by the ATP-sulfurylase enzyme, which results in the production of labeled-ATP and inorganic sulphate. In a second reaction, the luminescence reaction, luciferin and luciferase consume ATP as an energy source to generate light, AMP and oxyluciferin and to regenerate labeled pyrophosphate (PPi+FL) (FIG. 1D-1F). Thus, after each respective dNTP analog is incorporated, a quantum of light is generated for each molecule of labeled pyrophosphate (PPi+FL) in solution. In the course of the reactions for one embodiment contemplated herein, APS and luciferin are consumed and AMP and oxyluciferin are generated, while ATP sulfurylase and luciferase remain constant. The invention is not limited as to the type of luciferase used. Although certain disclosed embodiments utilized firefly luciferase, any luciferase known in the art may be used in the disclosed methods.

In accordance with the present invention, it has been found that Coenzyme A stabilizes the luciferase/luciferin couple or complex by preventing the degradation/deactivation of luciferase, which has the effect of increasing the intensity of signal of an ATP regenerating enzyme/luciferase amplification loop in a sequencing reaction. Accordingly, provided herein are methods of increasing the intensity of signal of an ATP regenerating enzyme/luciferase amplification loop in a sequencing reaction, comprising conducting the invention FLASH sequencing methods set forth herein; and adding Coenzyme A to the sequencing mixture, in a ratio of Coenzyme A to luciferase effective to increase the intensity of signal of an ATP regenerating enzyme/luciferase amplification loop Thus, in some embodiments, the amount of Conenzyme A used herein can be added to the invention sequencing mixture and solutions as a ratio of Coenzyme A:Luciferase, effective to increase the intensity of signal of an ATP regenerating enzyme/luciferase amplification loop in a sequencing reaction. In some embodiments, suitable Coenzyme A:Luciferase ratios contemplated for use herein can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 Coenzyme A:Luciferase, and the like. In other embodiments, suitable Luciferase:Coenzyme A ratios, effective to increase the intensity of signal of an ATP regenerating enzyme/luciferase amplification loop in a sequencing reaction, contemplated for use herein can be selected from the group consisting of: 1:1, 1:2, 1:5, 1:10, 1:20, 1:30, 1:40, 1:50, 1:60, 1:70, 1:80, 1:90, 1:100, 1:250, 1:150, 1:175, 1:200, 1:225, 1:250, 1:275, 1:300, 1:350, 1:400, 1:450, 1:500, 1:550, 1:600, 1:650, 1:700, 1:750, 1:800, 1:850, 1:900, 1:950, 1:1000, 1:1500, 1:2000, 1:3000, 1:4000, 1:5000 Luciferase:Coenzyme A, and the like.

As used herein a "polymerase enzyme" refers to the well-known protein responsible for carrying out nucleic acid synthesis. A preferred polymerase enzyme for use herein is a DNA polymerase. In natural polymerase mediated nucleic acid synthesis, a complex is formed between a polymerase enzyme, a template nucleic acid sequence, and a priming sequence that serves as the point of initiation of the synthetic process. During synthesis, the polymerase samples nucleotide monomers from the reaction mix to determine their complementarity to the next base in the template sequence. When the sampled base is complementary to the next base, it is incorporated into the growing nascent strand. This process continues along the length of the template sequence to effectively duplicate that template. Although described in a simplified schematic fashion, the actual biochemical process of incorporation can be relatively complex. A diagrammatical representation of the incorporation biochemistry is provided in FIG. 14. This diagram is not a complete description of the mechanism of nucleotide incorporation. During the reaction process, the polymerase enzyme undergoes a series of conformational changes which can be essential steps in the mechanism.

Figure 14:
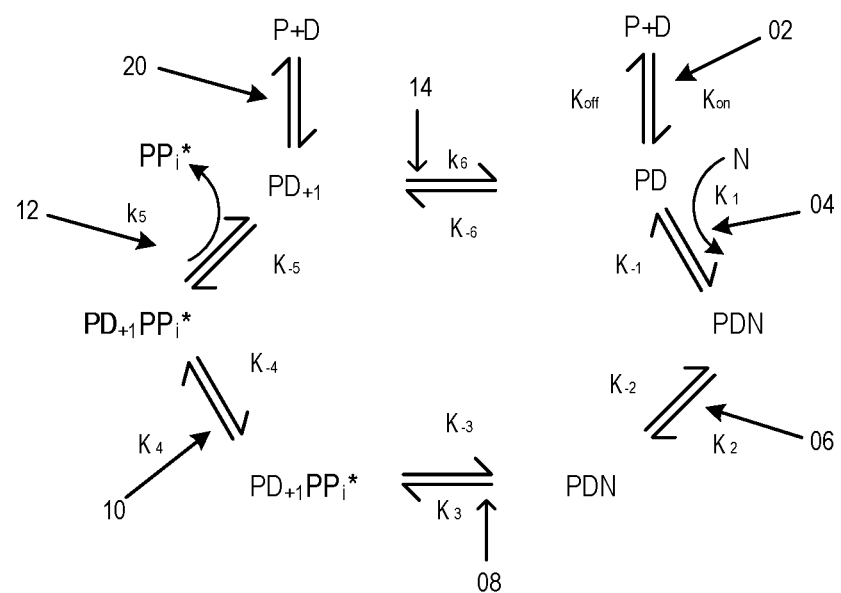
FIG. 14 shows a simplified schematic of the biochemical process of dNTP incorporation into a template strand.

As shown in FIG. 14, the synthesis process begins with the binding of the primed nucleic acid template (D) to the polymerase (P) at step 2. Nucleotide (N) binding with the complex occurs at step 4. Step 6 represents the isomerization of the polymerase from the open to closed conformation. Step 8 is the chemistry step in which the nucleotide is incorporated into the growing strand. At step 10, polymerase isomerization occurs from the closed to the open position. The polyphosphate component that is cleaved upon incorporation is released from the complex at step 12. While the figure shows the release of pyrophosphate, it is understood that when a labeled nucleotide or nucleotide analog is used, the component released may be different than pyrophosphate. In many cases, the systems and methods of the invention use a nucleotide analog having a label on its terminal phosphate, such that the released component comprises a polyphosphate connected to a dye (e.g., a label pyrophosphate; PP). With a natural nucleotide or nucleotide analog substrate, the polymerase then translocates on the template at step 14. After translocation, the polymerase is in the position to add another nucleotide and continue around the reaction cycle.

Suitable polymerase enzymes for use herein include DNA polymerases, which can be classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderrna pigmentosum variant (class Y). For a review of nomenclature, see, e.g., Burgers et al. (2001) "Eukaryotic DNA polymerases: proposal for a revised nomenclature" J Biol Chem. 276(47):43487-90. For a review of polymerases, see, e.g., Hubscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274: 17395-17398; each of which are incorporated herein by reference in their entirety. The basic mechanisms of action for many polymerases have been determined. The sequences of literally hundreds of polymerases are publicly available, and the crystal structures for many of these have been determined, or can be inferred based upon similarity to solved crystal structures for homologous polymerases.

Many such polymerases suitable for nucleic acid sequencing are readily available. For example, human DNA Polymerase Beta is available from R&D systems. Suitable DNA polymerase for use herein, include DNA polymerase I that is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. PHI.29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Other commercial DNA polymerases include PhusionhM High-Fidelity DNA Polymerase, available from New England Biolabs; GoTaq® Flexi DNA Polymerase, available from Promega; RepliPHI-™.PHI.29 DNA Polymerase, available from Epicentre Biotechnologies; PfuUltra™ Hotstart DNA Polymerase, available from Stratagene; KOD HiFi DNA Polymerase, available from Novagen; and many others.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to decrease branching fraction formation, improve stability of the closed polymerase-DNA complex, and/or alter reaction rate constants.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, PHI-29 related polymerases including wild type PHI-29 polymerase and derivatives of such polymerases such as exonuclease deficient forms, T7 DNA polymerase, T5 DNA polymerase, an RB69 polymerase, etc.

In addition, the polymerases can be further modified for application-specific reasons, such as to increase photostability, e.g., as taught in U.S. patent application Ser. No. 12/384,110 filed Mar. 30, 2009, to improve activity of the enzyme when bound to a surface, as taught, e.g., in WO 2007/075987, and WO 2007/076057, or to include purification or handling tags as is taught in the cited references and as is common in the art. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

Method of Achieving Long Read-Lengths in Single Molecule Reactions

The ability to achieve long read-lengths has been an elusive goal for existing sequencing methods. Every modern sequencing approach is limited in its ability to achieve long read-lengths. In particular, for single molecule sequencing methods this limitation comes from the relative affinity of the polymerase to the template DNA. During the sequencing reaction, polymerase will eventually fall from the template DNA thereby terminating the dNTP chain elongation reaction at that respective read length. For example with the Pacific Biosciences SMRT technology, there is one template and one polymerase per cell. For these single polymerase sequencing reactions, when the single polymerase dissociates from the template (falls away), the length of that particular read terminates, typically at relatively short read lengths corresponding to what is believed to be about 700 base pairs (bp).

Provided herein, in accordance with the present invention, are methods of sequencing a template nucleic acid, comprising:
   providing sequencing mixture comprising: a target template nucleic acid, a plurality of types of nucleotide analogs, and plurality of polymerase enzymes;
   carrying out nucleic acid synthesis such that a plurality of nucleotide analogs are added sequentially to the template; and
   detecting a respective nucleotide analog while nucleic acid synthesis is occurring, to determine a sequence of the template nucleic acid.

As used herein, the phrase "plurality of polymerase enzymes," "plurality of polymerases" or grammatical variations thereof, refers the number of polymerase enzymes used in a single sequencing reaction mixture. The quantity of polymerases in the "plurality of polymerase enzymes" can be selected from the group consisting of at least: 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 20000, 30000, 40000, 50000, 60000, 70000, 80000, 90000, 100000, 200000, 300000, 400000, 500000, 600000, 700000, 800000, 900000, and at least 1000000 polymerase enzymes. In other embodiments of continuously sequencing a target nucleic acid template, the ratio of polymerase to template is selected from the group consisting of at least 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1, 1000:1, 10000:1, 20000:1, 30000:1, 40000:1, 50000:1, 60000:1, 70000:1, 80000:1, 90000:1, 100000:1, 200000:1, 300000:1, 400000:1, 500000:1, 600000:1, 700000:1, 800000:1, 900000:1, and at least 1000000:1. The polymerases in the plurality can be a homogeneous collection of the same type of polymerase, or can be a heterogeneous collection of 2 or more different types of polymerases, e.g. 3, 4, 5, 6, 7, 8, 9, 10, 20, 30, 40, 50 up to 100 or more different polymerases in the plurality.

In one embodiment, the single sequencing reaction mixture has only one (a single) target template nucleic acid to be sequenced therein. In other embodiments, the single sequencing reaction mixture has more than one, or multiple, or a plurality of target template nucleic acid to be sequenced therein. In a particular embodiment, one target template nucleic acid is provided in an individual optical confinement.

Figure 9C:
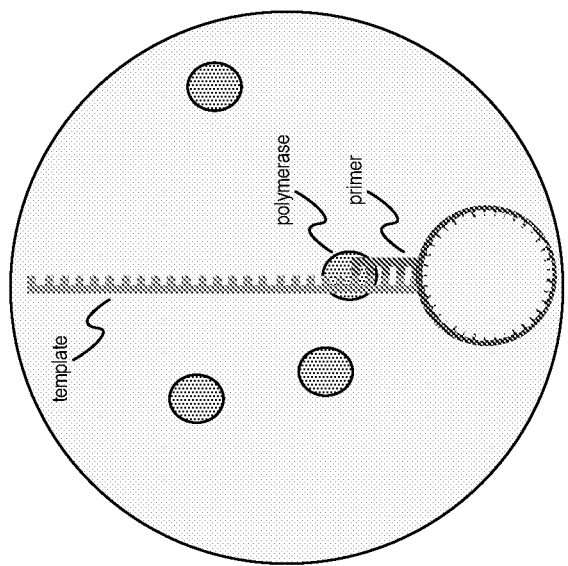
FIG. 9C shows an embodiment of confining the FLASH reaction reagents in a confinement area corresponding to a droplet; and shows a single self-priming target nucleic acid template in a sequence mixture having a plurality of polymerases.
Figure 9B:
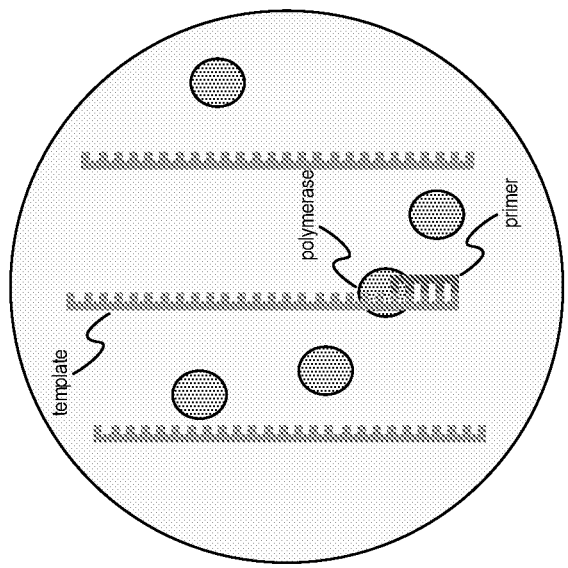
FIG. 9B shows an embodiment of confining the FLASH reaction reagents in a confinement area corresponding to a droplet; and shows a sequence mixture having plurality of target nucleic acid templates, a plurality of polymerases and a single primer, such that only a single target nucleic acid template is sequenced.
Figure 9A:
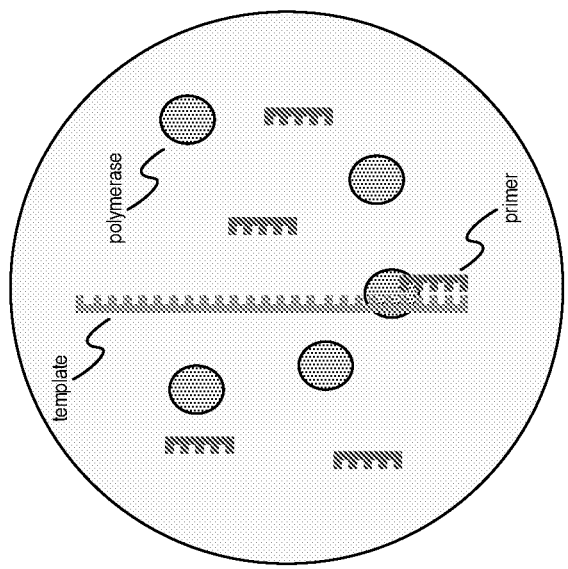
FIG. 9A shows an embodiment of confining the FLASH reaction reagents in a confinement area corresponding to a droplet; and shows a single target nucleic acid template in a sequence mixture having a plurality of polymerases and a plurality of primers.
Figure 12:
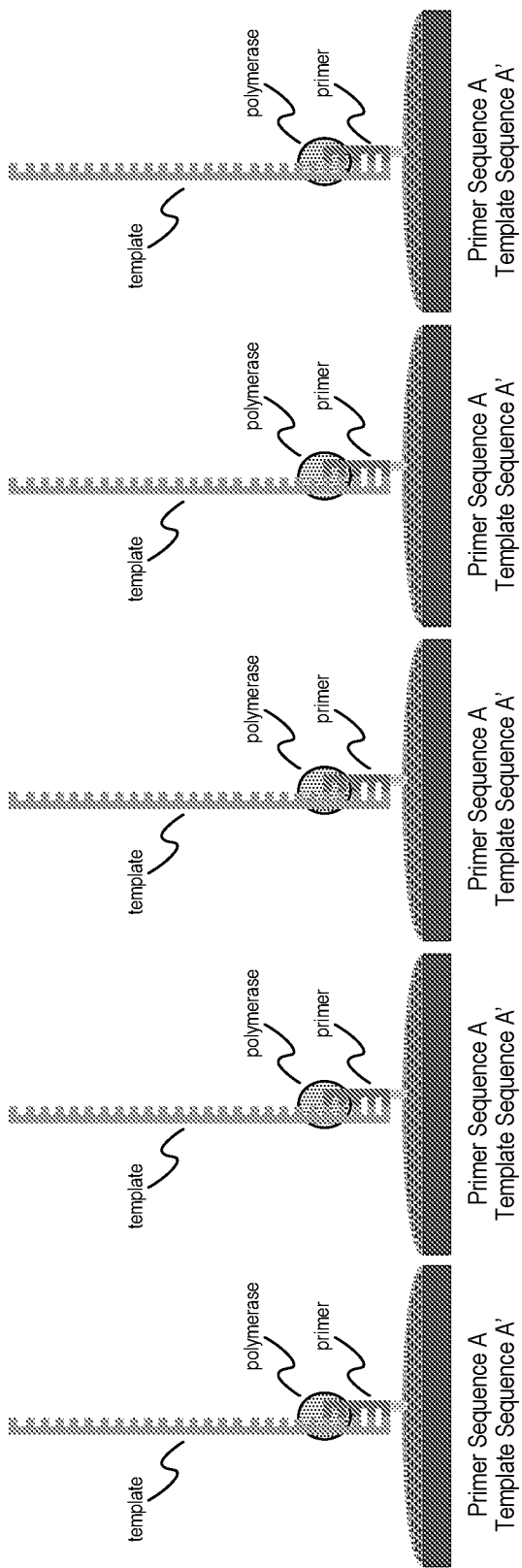
FIG. 12 shows an embodiment where numerous identical primers are bound to a substrate each at discreet loci, which can be in either a single overall reaction chamber, or in individual discreet reaction chambers. These primers bind essentially the same target template nucleic acid.

In some embodiments of the invention FLASH sequencing methods, the enzyme concatenate is provided in a particular individual confinement (e.g., a droplet, or the like), such that there is only one template target nucleic acid in the confinement area, while there is a plurality (e.g., many) of polymerase enzymes and a corresponding plurality of the other enzymes forming the concatenate (FIG. 9). In this embodiment, when a polymerase enzyme drops off (dissociates) from the target template nucleic acid (FIG. 11B), one of the many plurality of the other polymerases confined to the particular target nucleic acid template area, advantageously and relatively immediately commences its chain elongation at the location on the template where the previous polymerase left off or dissociated (FIG. 11B). In other words, the sequencing chain elongation occurs with a first polymerase enzyme until it gives way and dissociates from the template nucleic acid, then the sequencing chain elongation reaction continues with a second polymerase (different from the first) until it gives way and dissociates from the template nucleic acid, then the sequencing chain elongation reaction continues with a third polymerase (different from the second pol; which could be the first pol or another of the plurality of pols in the particular sequencing reaction) until it gives way and dissociates from the template nucleic acid, and so on. Those of skill in the art will readily understand that using this approach, the target nucleic acid template in continuously being sequenced, so long as the sequencing reaction is being run. Those of skill in the art will also readily understand that when using the substantially continuous method of sequencing disclosed herein, its read length is only limited by the length of the target nucleic and/or the physical size of the reaction confinement area used for the respective chain elongation reaction.

Accordingly, provided herein is a method of continuously sequencing a target nucleic acid template. In this embodiment, as used herein "continuity," "continuously sequencing a target nucleic acid template," or "substantially continuously sequencing a target nucleic acid template," does not mean that a single polymerase is able to continuously sequence a particular target nucleic acids for the entire long read lengths, but rather means that the plurality of polymerase enzymes in the reaction area of the target nucleic acid template, taken together between them, are able to continuously sequence a particular target, by virtue of that plurality of polymerase enzymes continuously having numerous polymerases available to take over dNTP chain elongation at the next nucleotide from where the previous polymerase dissociated from the particular target nucleic acid template.

In particular embodiments of invention continuous FLASH sequencing methods, especially where a plurality of polymerase are used to sequence a single target template nucleic acid, the overall read length is only limited by the length of target template nucleic acid that is provided to a particular reaction confinement area. For example, the overall read lengths contemplated herein that can be achieved by using a plurality of polymerases on a single target nucleic acid template, are up to the lengths of entire chromosomes, e.g., 50 million up to about 300 million base pairs (e.g, 300 Mbp), and the like. In other certain embodiments contemplated herein, read lengths achieved by the invention sequencing methods can be selected from the group consisting of at least: 200 bp, 300 bp, 400 bp, 500 bp, 600 bp, 700 bp, 800, bp, 900 bp, 1000 bp (i.e., 1 kbp), 5 kbp 10 kbp, 20 kbp, 30 kbp, 40 kbp, 50 kbp, 100 kbp, 200 kbp, 300 kbp, 400 kbp, 500 kbp, 600 kbp, 700 kbp, 800 kbp, 900 kbp, 1000 kbp (1 Mbp), 5 Mbp, 10 Mbp, 20 Mbp, 50 Mbp, 75 Mbp, 100 Mbp, 200 Mbp, 300 Mbp, 400 Mbp, 500 Mbp, 600 Mbp, 700 Mbp, 800 Mbp, 900 Mpb, 1000 Mbp.

Because of the substantially continuous sequencing of the target template nucleic acid by plurality of polymerases, the reaction is not limited by a single enzyme's ability to achieve a particular read length. This permits the use of enzymes with higher specificity and low error rates in the invention methods. In accordance with particular embodiments of the invention FLASH methods of sequencing, it is contemplated herein that using one template, and more than one polymerase (i.e., a plurality) can achieve infinitely long read-lengths. As set forth herein, as one polymerase falls off the target template nucleic acid, another polymerase will continue from where the previous polymerase left off, which advantageously alters the way the polymerase can be selected or optimized to perform in the invention FLASH methods of sequencing. For this reason, one of skill in the art can select a polymerase with a very low error rate, even though that polymerase may also have a relatively short read length. This provides an advantage for this particular embodiment, in that the polymerase selected for use in the invention sequencing methods does not require both long read length and specificity.

As used herein, the phrase "template nucleic acid" or "target template nucleic acid" refers to any suitable polynucleotide, including double-stranded DNA, single-stranded DNA, single-stranded DNA hairpins, DNA/RNA hybrids, RNAs with a recognition site for binding of the polymerizing agent, and RNA hairpins. Further, target polynucleotides suitable as template nucleic acids for use in the invention sequencing methods may be a specific portion of a genome of a cell, such as an intron, regulatory region, allele, variant or mutation; the whole genome; or any portion thereof. In other embodiments, the target polynucleotides may be mRNA, tRNA, rRNA, ribozymes, antisense RNA or RNAi. In other embodiments where only a single polymerase is contemplated for use to sequence a particular target, the target polynucleotide may be of any length, such as at between about 10 bases up to about 100,000 bases, between about 10,000 bases up to about 90,000 bases, between about 20,000 bases up to about 80,000 bases, between about 30,000 bases up to about 70,000 bases, between about 40,000 bases up to about 60,000 bases, or longer, with a typical range being between about 10,000-50,000 bases. Also contemplated herein, in this particular single polymerase embodiment, are target template nucleic acid lengths of between about 100 bases and 10,000 bases.

The template nucleic acids of the invention can also include unnatural nucleic acids such as PNAs, modified oligonucleotides (e.g., oligonucleotides comprising nucleotides that are not typical to biological RNA or DNA, such as 2'-O-methylated oligonucleotides), modified phosphate backbones and the like. A nucleic acid can be e.g., single-stranded or double-stranded.

As used herein, the phrase "nucleotide analog" refers to modified nucleotides that can be used in DNA synthesis (e.g., modified dNTPs such dATP, dTTP, dGTP, dCTP and dUTP). The nucleotide analogs for use in the invention can be any suitable nucleotide analog that is capable of being a substrate for the polymerase and for the selective cleaving activity. It has been shown that nucleotides can be modified and still used as substrates for polymerases and other enzymes. Where a variant of a nucleotide analog is contemplated, the compatibility of the nucleotide analog with the polymerase or with another enzyme activity such as exonuclease activity can be determined by activity assays. The carrying out of activity assays is straightforward and well known in the art.

The nucleotide analog can be, for example, a nucleoside polyphosphate having three or more phosphates in its polyphosphate chain with a label on the portion of the polyphosphate chain that is cleaved upon incorporation into the growing strand. The polyphosphate can be a pure polyphosphate, e.g. —O-PO3- or a pyrophosphate (e.g., PP), or the polyphosphate can include substitutions. Additional details regarding analogs and methods of making such analogs can be found in U.S. Pat. Nos. 7,405,281; 9,464,107, and the like; incorporated herein by reference in its entirety for all purposes.

Alternative labeling strategies may employ inorganic materials as labeling moieties, such as fluorescent or luminescent nanoparticles, e.g. nanocrystals, i.e. Quantum Dots, that possess inherent fluorescent capabilities due to their semiconductor make up and size in the nanoscale regime (See, e.g., U.S. Pat. Nos. 6,861,155, 6,699,723, 7,235,361, which are incorporated by reference herein for all purposes). Such nanocrystal materials are generally commercially available from, e.g., Life Technologies, (Carlsbad Calif.). Again, such compounds may be present as individual labeling groups or as interactive groups or pairs, e.g., with other inorganic nanocrystals or organic fluorophores. In some cases fluorescent proteins can be used such as green fluorescent protein (GFP, EGFP), blue fluorescent protein (EBFP, EBFP2, Azurite, mKalamal) cyan fluorescent protein (ECFP, Cerulean, CyPet) and yellow fluorescent protein derivatives (YFP, Citrine, Venus, YPet). Also contemplated for use herein is fluorescent cell barcoding using multipole fluorescence dyes procuding multiple color coded signals for detection, such as described in Krutzek et al., Curr Protoc Cytom. 2011 January; CHAPTER: Unit-6.31. (doi: 10.1002/0471142956.cy0631s55.); which is incorporated herein by reference in its entirety for all purposes.

In a preferred embodiment, the nucleotide analog is modified by adding a fluorophore to a terminal phosphate (see, e.g, Yarbrough et al., J. Biol. Chem., 254:12069-12073, 1979; incorporated herein by reference in its entirety for all purposes), such that when the PP, labeled leaving group (e.g., PPi+FL) is generated by the polymerase when the nucleotide analog is incorporated into the template strand, that labeled pyrophosphate is able to be combined with Adenosine 5' phosphosulfate by ATP Sulfurylase to form a labeled-ATP (ATP+FL) as shown in FIGS. 1B and 1C. There are four types of dNTPs, namely deoxyadenosine triphosphate (dATP), deoxyguanosine triphosphate (dGTP), deoxycytidine triphosphate (dCTP), and deoxythymidine triphosphate (dTTP). Instead of dATP, dATPaS might be used as a substitute for the dATP as it acts as a substrate for DNA polymerase but not for luciferase. In preferred embodiments of the invention methods disclosed herein, each respective dNTP is modified using a different, unique fluorophore relative to the other dNTPs, such that each time a polymerase incorporates a modified deoxyribonuleoside triphosphate (dNTP) nucleotide analog to the strand complementary to the template DNA, a fluorescence signal specific to the class or type of the nucleotide (e.g., unique signals for each of dATP, dATPaS, dTTP, dGTP and dCTP, or other modified nucleotides well-known in the art) attached is generated. Other modified nucleotides contemplated for use herein are well-known in the art such as those described in Jordheim et al., Advances in the development of nucleoside and nucleotide analogues for cancer and viral diseases, Nat. Rev. Drug Discov. (2013) 12: 447-464; and Guo et al. Four-color DNA sequencing with 3'-O-modified nucleotide reversible terminators and chemically cleavable fluorescent dideoxynucleotides, Proc. Natl. Acad. Sci. U.S.A. (2008) 105:9145-9150, and the like (each of which are incorporated by reference herein in their entirety).

In particular embodiments, exemplary nucleotide analogs, or labeled dNTPs, for use herein include:
gamma-(6-Aminohexyl)-2'-deoxyadenosine-5'-triphosphate, labeled with ATTO680, Triethylammonium;
gamma-(6-Aminohexyl)-2'-deoxycytidine-5'-triphosphate, labeled with ATTO680, Triethylammonium salt;
gamma-(6-Aminohexyl)-2'-deoxythymidine-5'-triphosphate, labeled with ATTO680, Triethylammonium salt;
gamma-[(6-Aminohexyl)imido]-dGTP-ATTO-647N;
gamma-[(6-Aminohexyl)imido]-dGTP—Cy5;
gamma-(6-Aminohexyl)-dGTP—Cy5;
gamma-(6-Aminohexyl)-2'-deoxythymidine-5'-triphosphate, labeled with Alexa700, Triethylammonium salt;
gamma-(6-Aminohexyl)-2'-deoxyadenosine-5'-triphosphate, labeled with Alexa660, Triethylammonium salt;
gamma-(6-Aminohexyl)-2'-deoxythymidine-5'-triphosphate, labeled with ATTO700, Triethylammonium salt; and the like.

In yet other embodiments, dATPaS, dGTPaS, dCTPaS, dTTPaS are used in place of dATP, dGTP, dCTP and dTTP, which is contemplated herein to reduce the non-specific interaction of nucleotides with enzymes other than polymerase (e.g., luciferase).

Each nucleotide effectively generates a unique fluorescence signal (e.g., in red, yellow, green, or blue, and the like) while they are being attached to the complementary strand by the polymerase enzyme. Upon the completion of attachment of the nucleotide analog to the 3' moiety of the previously attached nucleotide analog, as a result of the subsequent labeled-ATP and luminescence reactions the fluorescence generated by the labeled pyrophosphate leaving group (e.g., fluorescent pyrophosphate; PPi+FL) is detected by an appropriate fluorescence sensor and/or detection device during the discreet and limited period of the respective luminescence reactions (FIG. 1F).

Using the invention concatenated 3-Enzyme system and methods of Polymerase-ATP Sulfurylase-Luciferase provided herein, a particular signal indicating the particular type of nucleotide will be generated only during the specific interaction of the nucleotide with the polymerase-ATP Sulfurylase-Luciferasse. The pre- and post-polymerase interaction states will be similar; and the signal will "change" during the interaction with the polymerase. For example, in one embodiment described herein:

1—Initially because there is no external light excitation, there is either none or very low background fluorescence.
2-During the polymerase-ATP Sulfurylase-luciferase interaction of the invention methods, a specific type of fluorescence is generated.
3—After the respective luminescence reaction ceases the labeled pyrophosphate signal (PPi+FL) goes back to the initial state.

As used herein, the phrase "labeled leaving group" refers to the polyphosphate chain having a label, e.g., a fluorophore, or the like, attached therein, that is released from a respective dNTP when and/or upon cleavage by the invention 3 enzyme polymerase-ATP Sulfurylase-luciferase reaction during the incorporation of the respective dNTP into the template nucleic acid strand. In a particular embodiment herein, the polyphosphate is a fluorescently labeled pyrophosphate (PPi+FL) that is cleaved from dNTP (FIGS. 1A and 1B), converted to labeled ATP (ATP+FL; FIGS. 1B and 1C) and then subsequently released into the reaction mixture via the luciferase reaction (FIG. 1D-1F) for subsequent fluorescence detection prior to the termination of the respective, discreet, limited-period luminescence reaction as set forth herein (see FIG. 1F).

As set forth herein, this fluorescently labeled pyrophosphate (PPi+FL) can loop back to FIG. 1B numerous times in the ATP Sulfurylase/Luciferase Amplification Loop numerous time, prior to being converted (degraded) to Pi+Fl and Pi shown in FIG. 1G. The number of times fluorescently labeled pyrophosphate (PPi+FL) can be looped back to amplify the respective fluorescence signal for each dNTP incorporation into the elongating sequence can be selected from the group consisting of at least: 5, 10, 20, 30, 40, 50, 60, 70, 80, 90, 100, 150, 200, 250, 300, 350, 400, 450, 500, 550, 600, 650, 700, 750, 800, 850, 900, 950, 1000, 10000, 20000, 30000, 40000, 50000, 60000, 70000, 80000, 90000, 100000, 200000, 300000, 400000, 500000, 600000, 700000, 800000, 900000, and at least 1000000 times.

The reaction conditions used can also influence the relative rates of the various reactions. Thus, controlling the reaction conditions can be useful in ensuring that the sequencing method is successful at calling the bases within the template at a high rate. The reaction conditions include, e.g., the type and concentration of buffer, the pH of the reaction, the temperature, the type and concentration of salts, the presence of particular additives which influence the kinetics of the enzyme, and the type, concentration, and relative amounts of various cofactors, including metal cofactors. Manipulation of reaction conditions to achieve or enhance the two slow-step behavior of polymerases is described in detail in U.S. Pat. No. 8,133,672, incorporated herein by reference.

Enzymatic reactions are often run in the presence of a buffer, which is used, in part, to control the pH of the reaction mixture. The type of buffer can in some cases influence the kinetics of the polymerase reaction in a way that can lead to two slow-step kinetics, when such kinetics are desired. For example, in some cases, use of IRIS as buffer is useful for obtaining a two slow-step reaction. Suitable buffers include, for example, TAPS (3-{[tris(hydroxymethyl)methyl]amino}propanesulfonic acid), Bicine (N,N-bis(2-hydroxyethyl)glycine), IRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the kinetics of the polymerase reaction, and can be used as one of the polymerase reaction conditions to obtain a reaction exhibiting two slow-step kinetics. The pH can be adjusted to a value that produces a two slow-step reaction mechanism. The pH is generally between about 6 and about 9. In some embodiments, the pH is between about 6.5 and about 8.0. In other embodiments, the pH is between about 6.5 and 7.5. In particular embodiments, the pH is selected from about 6.5, 6.6, 6.7, 6.8, 6.9, 7.0, 7.1, 7.2, 7.3, 7.4, or 7.5.

The temperature of the reaction can be adjusted to ensure that the relative rates of the reactions are occurring in the appropriate range. The reaction temperature may depend upon the type of polymerase or selective cleaving activity employed. The temperatures used herein are also contemplated to manipulate and control the hydrogen bonding between two bases as well as the bases' interaction with the water in the reaction mixture, thereby controlling the solubility of the reaction components.

In some embodiments, additives, such as magnesium, Coenzyme A, and the like, can be added to the reaction mixture that will influence the kinetics of the reaction. In some cases, the additives can interact with the active site of the enzyme, acting for example as competitive inhibitors. In some cases, additives can interact with portions of the enzyme away from the active site in a manner that will influence the kinetics of the reaction. Additives that can influence the kinetics include, for example, competitive but otherwise unreactive substrates or inhibitors in analytical reactions to modulate the rate of reaction as described in U.S. Pat. No. 8,252,911, the full disclosure of which is incorporated herein by reference in its entirety for all purposes.

As another example, an isotope such as deuterium can be added to influence the rate of one or more step in the polymerase reaction. In some cases, deuterium can be used to slow one or more steps in the polymerase reaction due to the deuterium isotope effect. By altering the kinetics of steps of the polymerase reaction, in some instances two slow step kinetics, as described herein, can be achieved. The deuterium isotope effect can be used, for example, to control the rate of incorporation of nucleotide, e.g., by slowing the incorporation rate. Isotopes other than deuterium can also be employed, for example, isotopes of carbon (e.g. $^{13}C$), nitrogen, oxygen, sulfur, or phosphorous.

As yet another example, additives that can be used to control the kinetics of the polymerase reaction include the addition of organic solvents. The solvent additives are generally water soluble organic solvents. The solvents need not be soluble at all concentrations, but are generally soluble at the amounts used to control the kinetics of the polymerase reaction. While not being bound by theory, it is believed that the solvents can influence the three dimensional conformation of the polymerase enzyme which can affect the rates of the various steps in the polymerase reaction. For example, the solvents can affect steps involving conformational changes such as the isomerization steps. Added solvents can also affect, and in some cases slow, the translocation step. In some cases, the solvents act by influencing hydrogen bonding interactions.

The water miscible organic solvents that can be used to control the rates of one or more steps of the polymerase reaction in single molecule sequencing include, e.g., alcohols, amines, amides, nitriles, sulfoxides, ethers, and esters and small molecules having more than one of these functional groups. Exemplary solvents include alcohols such as methanol, ethanol, propanol, isopropanol, glycerol, and small alcohols. The alcohols can have one, two, three, or more alcohol groups. Exemplary solvents also include small molecule ethers such as tetrahydrofuran (THF) and dioxane, dimethylacetamide (DMA), dimethylsulfoxide (DMSO), dimethylformamide (DMF), and acetonitrile.

The water miscible organic solvent can be present in any amount sufficient to control the kinetics of the polymerase reaction. The solvents are generally added in an amount less than 40% of the solvent weight by weight or volume by volume. In some embodiments the solvents are added between about 0.1% and 30%, between about 1% and about 20%, between about 2% and about 15%, and between about 5% and 12%. The effective amount for controlling the kinetics can be determined by the methods described herein and those known in the art.

Another aspect of controlling the polymerase reaction conditions relates to the selection of the type, level, and relative amounts of cofactors. For example, during the course of the polymerase reaction, divalent metal co-factors, such as magnesium or manganese, will interact with the enzyme-substrate complex, playing a structural role in the definition of the active site. For a discussion of metal co-factor interactions in polymerase reactions, see, for example, Arndt, et al., Biochemistry (2001) 40:5368-5375. Suitable conditions include those described in U.S. Pat. No. 8,257,954, incorporated herein by reference in its entirety for all purposes.

In a particular embodiment of the invention methods, the rate and fidelity of the polymerase reaction is controlled by adjusting the concentrations of the dNTP nucleotide analogs such that the polymerase operates in near ideal conditions in terms of parameters such as substrate concentration, amount of optical excitation, level of chemical modification. Therefore, the polymerase enzyme is contemplated herein to reach its maximum read-lengths, e.g., approximately in the tens of thousands of base pairs, similar to the DNA synthesis lengths achieved in natural settings. This reduces device complexity and increases enzymatic sensitivity and specificity leading to low error-rates and thus low coverage. This not only reduces the cost of the device as well as cost per genome, but also makes applications such as single-nucleotide polymerism detection, structural variation, and genome assembly possible in a very compact system.

In another embodiment, as set forth above, because the labeled-ATP enzyme (e.g., ATP sulfurylase) and polymerase rates can vary significantly depending on the type and source of the enzymes, the rate of labeled-ATP production by the ATP sulfurylase reaction employed herein can be adjusted separately by adjusting reaction conditions such as ATP sulfurylase concentration.

The invention includes systems for sequencing of nucleic acid templates. The systems provide for concurrently sequencing a plurality of nucleic acid templates. The system can incorporate all of the reagents and methods described herein, and provides the instrumentation required for containing the sample, illuminating the sample with excitation light from the luminescence reactions, detecting light emitted from the sample during sequencing to produce intensity versus time data from the labeled leaving groups (e.g, PPi+FL) cleaved from the labeled-ATP analogs as the respective dNTPs are incorporated by the polymerase onto its cognate template dna; and from the respective labeled leaving groups, e.g., fluorophore-labeled pyrophosphate, determining the sequence of a template using the sequential intensity versus time data.

As used herein, the phrase "detecting light" refers to well-known methods for detecting, for example, fluorescence emitted from fluorophore labels when such labels are in their excitation state emitting their respective signal.

As used herein a "pyrophosphatase enzyme" refers to the well known protein responsible for catalyzing the hydrolysis of pyrophosphate into to 2 phosphate ions. A exemplary pyrophosphatase enzyme for use herein is the human pyrophosphatase described in U.S. Pat. No. 5,843,665; and bovine pyrophosphatase described in Yang, Z and Wensel, T G (1992) J Biol Chem 267: 24634-40, 24641-7; each of which are incorporated by reference in their entirety.

As use herein, the term "ATP regenerating enzyme/ Luciferase loop" or grammatical variations thereof (e.g., ATP Sulfurylase/Luciferase loop, AGPPase/Luciferase loop, PPDK/luciferase loop, and the like), refers to generally as an enzymatic loop between the ATP regenerating enzyme and luciferase (FIG. 1B-1G), whereby following the luminescent reaction catalyzed by luciferase a new pyrophosphate molecule is released still having the fluorescent label attached (PPi+FL) (FIG. 1.F). This newly released PPi-FL can once again be a substrate for the ATP regenerating enzyme (e.g., ATP Sulfurylase, AGPPase, PPDK, and the like) thereby generating an enzymatic loop between ATP regenerating enzyme (e.g., ATP Sulfurylase, AGPPase, PPDK, and the like) and luciferase (FIG. 1G.Top). As shown in FIG. 1B-1G, withing this loop PPi+FL is recycled by ATP Sulfurylase and converted into fluorescently labeled ATP (ATP-FL), which can then be catalyzed by luciferase releasing PPi-FL. This will generate successive signals from the labeled pyrophosphate, and thereby serve as an amplification mechanism for the sequencing signal for the most recent nucleotide.

As used herein, the term "co-encapsulated," encapsulate or grammatical variations thereof refers to the incorporation of 2 or more enzymes, such as luciferase and pyrophosphatase (inorganic), into a capsule (e.g., nanomatrix or nanoparticle), such as a mesoporous nanomatrix set forth herein.

As used herein, the term "nanomatrix" refers to a nanoscale coating, structure or vessel typically comprised of a biocompatible or polymer material forming an enclosed structure that is able to encapsulate enzymes and reactants within a confined space. The nanomatrix is not permeable to all molecules, but instead only a desired subset of molecules can pass through its walls or membrane. For example, the nanomatrix confines enzymes to a particular space within a reaction mixture such that certain reactions are only able to occur within the nanomatrix encapsulating the particular enzymes. In one embodiment, the enzymes encapsulated are luciferase and pyrophosphatase (e.g., inorganic and the like). An exemplary nanomatrix for use herein is set forth in, for example, US 201/0067191A1 and Zhou et al., Acta Pharmaceutica Sinica B (2018), www//dli.org/10/1016/ j.apsb.2018.01.007; and includes nanoparticles (e.g., mesoporous silica nanoparticles), and the like. The nanomatrix and/or nanoparticle can carry a charge as described in US 2016/0067191A1, which is incorporated by reference herein in its entirety. In one embodiment, the nanomatrix is a nanoparticle that is negatively charged.

In one embodiment, the system for sequencing generally comprises a substrate having a plurality of single polymerase enzymes, single templates, or single primers within, for example, a unique droplet, or the like. In the case of highly processive enzyme polymerase reactions, each comprising a polymerase enzyme, a nucleic acid template, and a primer are uniquely confined such that their signals can be assigned to the respective nucleotide as gene synthesis occurs. In other embodiments provided herein a plurality of polymerase enzymes are used with a single templates and/or a single primer, within, for example, a unique confinement, droplet, or the like. The sequencing reagents generally include two or more types of nucleotide analogs, preferably four nucleotide analogs corresponding dATP, dTTP, dAGP and dCTP, each nucleotide analog labeled with a different label. The polymerase sequentially adds nucleotides or nucleotide analogs to the growing strand, which extends from the primer. Each added nucleotide or nucleotide analog is complementary to the corresponding base on the template nucleic acid, such that the portion of the growing strand that is produced is complementary to the template.

The system comprises luminescence reagents (e.g., firefly luciferase and luciferin) for illuminating the labeled pyrophosphate leaving groups from the respective dNTPs as they are incorporated into the template strand and further undergo the labeled-ATP reaction (via ATP-sulfurylase) and luminescence reaction (e.g., firefly luciferase+luciferin) as set forth in FIGS. 1B-1F. The luminescence reaction illuminates the respective labeled leaving groups in a wavelength range that will excite the labels on the cleaved labeled pyrophosphates (no longer bound to the labeled ATP)(See FIGS. 1E and 1F).

The system further comprises detection optics for observing signals from the labeled leaving groups cleaved from the respective labeled-ATP (ATP+FL; corresponding to a respective dNTP) during the polymerase enzyme mediated addition to the template strand. The detection optics observe a plurality of single molecule polymerase sequencing reactions concurrently, observing the nucleotide or nucleotide analog additions for each of them via the labeled leaving group (e.g., fluorophore-labeled pyrophosphate; PP) that is ultimately cleaved from the labeled-ATP in the invention concatenated 3 enzyme (Polymerase-ATP Sulfurylase-Luciferase) system. For each of the observed single molecule polymerase sequencing reactions, the detection optics concurrently observe the signals from each of the labeled leaving groups that are indicative of the respective fluorophore-label that is excited by the respective luminescence reaction corresponding to a respective dNTP, until each discreet and limited period, respective signal ceases due to the decay and termination of the luminescent signal from the respective luminescence (e.g., luciferase/luciferin) reaction.

The system also comprises a computer configured to determine the type of nucleotide analog that is added to the growing strand using the observed signal from the respective leaving group; whereby observed signals from the labeled leaving group are used to indicate whether a type of nucleotide or nucleotide analog is incorporated into the growing strand. The computer generally receives information regarding the observed signals from the detection optics in the form of signal data. The computer stores, processes, and interprets the signal data, using the signal data in order to produce a sequence of base calls. The base calls represent the computers estimate of the sequence of the template from the signal data received combined with other information given to the computer to assist in the sequence determination.

Optical detections systems which can be used with the present invention are described, for example in U.S. Pat. Nos. 8,802,424; 7,714,303; and 7,820,983, each of which are incorporated herein by reference in their entirety for all purposes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems, Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other sequencing specific formats including "fastq" or the "qseq" format (Illumina); while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

In some embodiments of the methods and systems of the invention, optical confinements are used to enhance the ability to concurrently observe multiple single molecule polymerase sequencing reactions simultaneously. In general, optical confinements are disposed upon a substrate and used to provide electromagnetic radiation to or derive such radiation from only very small spaces or volumes. Such optical confinements may comprise structural confinements, e.g., wells, recesses, conduits, or the like, or they may comprise optical processes in conjunction with other components, to provide detection or derive emitted radiation from only very small volumes. Examples of such optical confinements include systems that utilize, e.g., total internal reflection (TIR) based optical systems whereby light is directed through a transparent portion of the substrate at an angle that yields total internal reflection within the substrate.

In a particular embodiment, a preferred optical confinement is a micro-droplet (e.g., water-in-oil emulsion, and the like) which can contain and individual sequencing reaction set forth herein. For example, the sequencing mixture reaction ingredients can be split in a way that each micro-droplet contains one polymerase-ATP Sulfurylase-luciferase set of enzymes and related reagents and one template nucleic acid whereby each signal detection unit is focused on a single micro-droplet. It is contemplated herein that each micro-droplet is a single molecule reaction cell containing individual single molecule sequencing reactions. The micro-droplet reaction cell is also advantageously useful in the invention sequencing methods to act as micro-lenses to focus light on the respective signal detection unit.

The substrates of the invention are generally rigid, and often planar, but need not be either. Where the substrate comprises an array of optical confinements, the substrate will generally be of a size and shape that can interface with optical instrumentation to allow for the illumination and for the measurement of light from the optical confinements. Typically, the substrate will also be configured to be held in contact with liquid media, for instance containing reagents and substrates and/or labeled components, such as the fluorophore-labeled pyrophosphates, for optical measurements.

Exemplary embodiments for providing the components of invention sequencing mixture in a confinement area include among numerous other configurations, those that are shown in FIGS. 9-13. For example, in one embodiment, each target nucleic acid template is bound to the surface of an individual respective signal detector. In one embodiment, the nucleic acid template can be directly bound or attached to the surface or solid substrate using numerous methods well-known in the art, such as for example, via a thiol bond to a gold surface, or the like (FIG. 10B). In other embodiments, DNA templates can be directly bound or attached to a respective surface, via silanes, an NHS ester, or the like. In other embodiments, primers for sequencing can be bound to the surface of an individual respective signal detector (FIG. 10A). As set forth herein, each attachment can be on a surface of a individual signal detector. Exemplary signal detectors have been described herein, and can be pixels of a CCD, CMOS sensor, or they can be a photodetector, or photomultiplier forming an array, or the like.

Where the substrates comprise arrays of optical confinements, the arrays may comprise a single row or a plurality of rows of optical confinement on the surface of a substrate, where when a plurality of lanes are present, the number of lanes will usually be at least 2, more commonly more than 10, and more commonly more than 100. The subject array of optical confinements may align horizontally or diagonally long the x-axis or the y-axis of the substrate. The individual confinements can be arrayed in any format across or over the surface of the substrate, such as in rows and columns so as to form a grid, or to form a circular, elliptical, oval, conical, rectangular, triangular, or polyhedral pattern. To minimize the nearest-neighbor distance between adjacent optical confinements, a hexagonal array is sometimes preferred.

The array of optical confinements may be incorporated into a structure that provides for ease of analysis, high throughput, or other advantages, such as in a microtiter plate and the like. Such setup is also referred to herein as an "array of arrays." For example, the subject arrays can be incorporated into another array such as microtiter plate wherein each micro well of the plate contains a subject array of optical confinements.

In accordance with the invention, arrays of confinements (e.g., reaction cells, micro-droplets, and the like) are provided in arrays of more than 100, more than 1000, more than 10,000, more than 100,000, or more than 1,000,000 separate reaction cells (such as a micro-droplet or the like) on a single substrate. In addition, the reaction cell arrays are typically comprised in a relatively high density on the surface of the substrate. Such high density typically includes reaction cells present at a density of greater than 10 reaction cells per $mm^2$, preferably, greater than 100 reaction cells per $mm^2$ of substrate surface area, and more preferably, greater than 500 or even 1000 reaction cells per $mm^2$ and in many cases up to or greater than 100,000 reaction cells per mm $mm^2$. Although in many cases, the reaction cells in the array are spaced in a regular pattern, e.g., in 2, 5, 10, 25, 50 or 100 or more rows and/or columns of regularly spaced reaction cells in a given array, in certain preferred cases, there are advantages to providing the organization of reaction cells in an array deviating from a standard row and/or column format. In preferred aspects, the substrates include as the particular reaction cell micro-droplets as the optical confinements to define the discrete single molecule sequencing reaction regions on the substrate.

The overall size of the array of optical confinements can generally range from a few nanometers to a few millimeters in thickness, and from a few millimeters to 50 centimeters in width and/or length. Arrays may have an overall size of about few hundred microns to a few millimeters in thickness and may have any width or length depending on the number of optical confinements desired.

The spacing between the individual confinements can be adjusted to support the particular application in which the subject array is to be employed. For instance, if the intended application requires a dark-field illumination of the array without or with a low level of diffractive scattering of incident wavelength from the optical confinements, then the individual confinements may be placed close to each other relative to the incident wavelength.

The individual confinement in the array can provide an effective observation volume less than about 1000 zeptoliters, less than about 900, less than about 200, less than about 80, less than about 10 zeptoliters. Where desired, an effective observation volume less than 1 zeptoliter can be provided. In a preferred aspect, the individual confinement yields an effective observation volume that permits resolution of individual molecules, such as enzymes, present at or near a physiologically relevant concentration. The physiologically relevant concentrations for many biochemical reactions range from micro-molar to millimolar because most of the enzymes have their Michaelis constants in these ranges. Accordingly, preferred array of optical confinements has an effective observation volume for detecting individual molecules present at a concentration higher than about 1 micromolar (uM), or more preferably higher than 50 uM, or even higher than 100 uM. In particular embodiments, typical microdroplet sizes range from 10 micrometers to 200 micrometers, and thus typical microdroplet volumes are around 5 picoliters to 20 nanoliters.

In the context of chemical or biochemical analyses within optical confinements, it is generally desirable to ensure that the reactions of interest are taking place within the optically interrogated portions of the confinement, at a minimum, and preferably such that only the reactions of a single molecule polymerase sequencing reaction is occurring within an interrogated portion of an individual confinement (e.g., within a micro-droplet, or the like). A number of methods well-known in the art may generally be used to provide individual molecules within the observation volume. A variety of these are described in U.S. Pat. No. 7,763,423, incorporated herein by reference in its entirety for all purposes, which describes, inter alia, modified surfaces that are designed to immobilize individual molecules to the surface at a desired density, such that approximately one, two, three or some other select number of molecules would be expected to fall within a given observation volume. Typically, such methods utilize dilution techniques to provide relatively low densities of coupling groups on a surface, either through dilution of such groups on the surface or dilution of intermediate or final coupling groups that interact with the molecules of interest, or combinations of these. Also contemplated herein is the use of these dilution techniques for providing one, two, three or some other select number of single molecule sequencing reactions to fall within a given observation volume without being immobilized to a surface, such as would occur in the micro-droplet reaction cell contemplated herein for optical confinement. In a particular embodiment, the dilution techniques are utilized to provide a single molecule sequencing reaction in a micro-droplet for use in the invention sequencing method.

The systems and methods of the inventions can result in improved sequence determination and improved base calling by monitoring the signal from the labeled leaving groups of the nucleotide analogs after undergoing the 3 enzyme pol-ATP sulfurylase-luciferase set forth herein (e.g., a polyphosphate label; PPi+FL) using systems well-known in the art. In general, signal data is received by the processor. The information received by the processor can come directly from the detection optics, or the signal from the detection optics can be treated by other processors before being received by the processor. A number of initial calibration operations may be applied. Some of these initial calibration steps may be performed just once at the beginning of a run or on a more continuous basis during the run. These initial calibration steps can include such things as centroid determination, alignment, gridding, drift correction, initial background subtraction, noise parameter adjustment, frame-rate adjustment, etc. Some of these initial calibration steps, such as binning, may involve communication from the processor back to the detector/camera, as discussed further below.

Generally, some type of spectral trace determination, spectral trace extraction, or spectral filters are applied to the initial signal data. Some or all of these filtration steps may optionally be carried out at a later point in the process, e.g., after the pulse identification step. The spectral trace extraction/spectral filters may include a number of noise reduction and other filters as is well-known in the art. Spectral trace determination is performed at this stage for many of the example systems discussed herein because the initial signal data received are the light levels, or photon counts, captured by a series of adjacent pixel detectors. For example, in one example system, pixels (or intensity levels) from positions are captured for an individual wave-guide at each frame. Light of different frequencies or spectrum will fall on more than one of the positions and there is generally some overlap and possibly substantial overlap. According to specific embodiments of the invention, spectral trace extraction may be performed using various type of analyses, as discussed below, that provide the highest signal-to-noise ratio for each spectral trace.

As an alternative to a spectral trace determination, methods of the invention may also analyze a single signal derived from the intensity levels at the multiple pixel positions (this may be referred to as a summed spectral signal or a gray-scale spectral signal or an intensity level signal). In many situations, it has been found that spectral extraction, however, provides better SNR (signal to noise ratio) and therefore pulse detection when extracted spectral traces are analyzed for pulses somewhat separately. In further embodiments, a method according to the invention may analyze the multiple captured pixel data using a statistical model such as a Hidden Markov Model. In the invention sequencing methods and systems provided herein, determining multiple (e.g., four) spectral traces from the initial signal data is a preferred method.

Whether the signal from the labeled leaving groups (e.g., labeled-pyrophosphates; PPi+FL) can be categorized as a significant signal pulse or event is determined. In some example systems, because of the small number of photons available for detection and because of the speed of detection, various statistical analysis techniques may be performed in determining whether a significant pulse has been detected.

If the signal is identified as a significant pulse or signal event, a further optional spectral profile comparison may be performed to verify the spectral assignment. This spectral profile comparison is optional in embodiments where spectral traces are determined prior to or during pulse identification. Once a color is assigned to a given incorporation signal (e.g., a fluorophore-labeled dNTP), that assignment is used to call either the respective base incorporated, or its complement in the template sequence. In order to make this determination, the signals coming from the channel corresponding to the labeled leaving group (e.g., labeled-pyrophosphates; PPi+FL) are used to assess whether a pulse from a nucleotide label corresponds to an incorporation event. The compilation of called bases is then subjected to additional processing to provide linear sequence information, e.g., the successive sequence of nucleotides in the template sequence, assemble sequence fragments into longer contigs, or the like.

As noted above, the signal data is input into the processing system, e.g., an appropriately programmed computer or other processor. Signal data may input directly from a detection system, e.g., for real time signal processing, or it may be input from a signal data storage file or database. In some cases, e.g., where one is seeking immediate feedback on the performance of the detection system, adjusting detection or other experimental parameters, real-time signal processing will be employed. In some embodiments, signal data is stored from the detection system in an appropriate file or database and is subject to processing in post reaction or non-real time fashion.

The signal data used in conjunction with the present invention may be in a variety of forms. For example, the data may be numerical data representing intensity values for optical signals received at a given detector or detection point of an array based detector. Signal data may comprise image data from an imaging detector, such as a CCD, EMCCD, ICCD or CMOS sensor. In particular embodiments, for detecting low numbers of photons from single molecules, the use of a photomultiplier tube (PMT) and/or a photon counter unit is contemplated for use in the invention methods. In either event, signal data used according to specific embodiments of the invention generally include both intensity level information and spectral information. In the context of separate detector elements, such spectral information will generally includes identification of the location or position of the detector portion (e.g., a pixel) upon which an intensity is detected. In the context of image data, the spectral image data will typically be the data derived from the image data that correlates with the calibrated spectral image data for the imaging system and detector when the system includes spectral resolution of overall signals. The spectral data may be obtained from the image data that is extracted from the detector, or alternatively, the derivation of spectral data may occur on the detector such that spectral data will be extracted from the detector.

For the sequencing methods described above, there may be a certain amount of optical signal that is detected by the detection system that is not the result of a signal from an incorporation event. Such signal will represent "noise" in the system, and may derive from a number of sources that may be internal to the monitored reaction, internal to the detection system and/or external to all of the above. The practice of the present invention advantageously reduces these overall sources of noise typically present in prior art methods. Examples of prior art noise internal to the reaction that is advantageously reduced in accordance with the present invention includes, e.g.: presence of fluorescent labels that are not associated with a detection event, e.g., liberated labels, labels associated with unincorporated bases in diffused in solution, bases associated with the complex but not incorporated; presence of multiple complexes in an individual observation volume or region; non-specific adsorption of dyes or nucleotides to a substrate or enzyme complex within an observation volume; contaminated nucleotide analogs, e.g., contaminated with other fluorescent components; other reaction components that may be weakly fluorescent; spectrally shifting dye components, e.g., as a result of reaction conditions; and the like. The controlled use of fluorescent signal detection and information from the fluorescent label on the leaving group of the respective dNTP that undergoes a discreet, limited-period Polymerase-ATP-sulfurylase-Luciferase reaction prior to the incorporation of the next nucleotide analog advantageously provides a way of reducing or eliminating sources of noise, thereby improving the signal to noise of the system, and improving the quality of the base calls and associated sequence determination.

Sources of noise internal to the detection system, but outside of the reaction mixture can include, e.g., reflected excitation radiation that bleeds through the filtering optics; scattered excitation or fluorescent radiation from the substrate or any of the optical components; spatial cross-talk of adjacent signal sources; auto-fluorescence of any or all of the optical components of the system; read noise from the detector, e.g., CCDs, gain register noise, e.g., for EMCCD cameras, and the like. Other system derived noise contributions can come from data processing issues, such as background correction errors, focus drift errors, autofocus errors, pulse frequency resolution, alignment errors, and the like. Still other noise contributions can derive from sources outside of the overall system, including ambient light interference, dust, and the like.

These noise components contribute to the background photons underlying any signal pulses that may be associated with an incorporation event. As such, the noise level will typically form the limit against which any signal pulses may be determined to be statistically significant.

Identification of noise contribution to overall signal data may be carried out by a number of methods well-known in the art, including, for example, signal monitoring in the absence of the reaction of interest, where any signal data is determined to be irrelevant. Alternatively, and preferably, a baseline signal is estimated and subtracted from the signal data that is produced by the system, so that the noise measurement is made upon and contemporaneously with the measurements on the reaction of interest. Generation and application of the baseline may be carried out by a number of means, which are described in greater detail below.

In accordance with the present invention, signal processing methods distinguish between noise, as broadly applied to all non-significant pulse-based signal events, and significant signal pulses that may, with a reasonable degree of confidence, be considered to be associated with, and thus can be tentatively identified as, an incorporation event. In the context of the present invention, a signal event is first classified as to whether it constitutes a significant signal pulse based upon whether such signal event meets any of a number of different pulse criteria. Once identified or classified as a significant pulse, the signal pulse may be further assessed to determine whether the signal pulse constitutes an incorporation event and may be called as a particular incorporated base. As will be appreciated, the basis for calling a particular signal event as a significant pulse, and ultimately as an incorporation event, will be subject to a certain amount of error, based upon a variety of parameters as generally set forth herein. As such, it will be appreciated that the aspects of the invention that involve classification of signal data as a pulse, and ultimately as an incorporation event or an identified base, are subject to the same or similar errors, and such nomenclature is used for purposes of discussion and as an indication that it is expected with a certain degree of confidence that the base called is the correct base in the sequence, and not as an indication of absolute certainty that the base called is actually the base in a given position in a given sequence.

One such signal pulse criterion is the ratio of the signals associated with the signal event in question to the level of all background noise ("signal to noise ratio" or "SNR"), which provides a measure of the confidence or statistical significance with which one can classify a signal event as a significant signal pulse. In distinguishing a significant pulse signal from systematic or other noise components, the signal generally must exceed a signal threshold level in one or more of a number of metrics, including for example, signal intensity, signal duration, temporal signal pulse shape, pulse spacing, and pulse spectral characteristics.

By way of a simplified example, signal data may be input into the processing system. If the signal data exceeds a signal threshold value in one or more of signal intensity and signal duration, it may be deemed a significant pulse signal. Similarly, if additional metrics are employed as thresholds, the signal may be compared against such metrics in identifying a particular signal event as a significant pulse. As will be appreciated, this comparison will typically involve at least one of the foregoing metrics, and preferably at least two such thresholds, and in many cases three or all four of the foregoing thresholds in identifying significant pulses.

Signal threshold values, whether in terms of signal intensity, signal duration, pulse shape, spacing or pulse spectral characteristics, or a combination of these, will generally be determined based upon expected signal profiles from prior experimental data, although in some cases, such thresholds may be identified from a percentage of overall signal data, where statistical evaluation indicates that such thresholding is appropriate. In particular, in some cases, a threshold signal intensity and/or signal duration may be set to exclude all but a certain fraction or percentage of the overall signal data, allowing a real-time setting of a threshold. Again, however, identification of the threshold level, in terms of percentage or absolute signal values, will generally correlate with previous experimental results. In alternative aspects, the signal thresholds may be determined in the context of a given evaluation. In particular, for example, a pulse intensity threshold may be based upon an absolute signal intensity, but such threshold would not take into account variations in signal background levels, e.g., through reagent diffusion, that might impact the threshold used, particularly in cases where the signal is relatively weak compared to the background level. As such, in certain aspects, the methods of the invention determine the background fluorescence of the particular reaction in question, which is relatively small because the contribution of freely diffusing dyes or dye labeled analogs into a micro-droplet is minimal or non-existent, and sets the signal threshold above that actual background by the desired level, e.g., as a ratio of pulse intensity to background fluorophore diffusion, or by statistical methods, e.g., 5 sigma, or the like. By correcting for the actual reaction background, such as the minimal fluorophore diffusion background, the threshold is automatically calibrated against influences of variations in dye concentration, laser power, or the like. By reaction background is meant the level of background signal specifically associated with the reaction of interest and that would be expected to vary depending upon reaction conditions, as opposed to systemic contributions to background, e.g., autofluorescence of system or substrate components, laser bleedthrough, or the like.

In particularly preferred aspects that rely upon real-time detection of incorporation events, identification of a significant signal pulse may rely upon a signal profile that traverses thresholds in both signal intensity and signal duration. For example, when a signal is detected that crosses a lower intensity threshold in an increasing direction, ensuing signal data from the same set of detection elements, e.g., pixels, are monitored until the signal intensity crosses the same or a different intensity threshold in the decreasing direction. Once a peak of appropriate intensity is detected, the duration of the period during which it exceeded the intensity threshold or thresholds is compared against a duration threshold. Where a peak comprises a sufficiently intense signal of sufficient duration, it is called as a significant signal pulse.

In addition to, or as an alternative to using the intensity and duration thresholds, pulse classification may employ a number of other signal parameters in classifying pulses as significant. Such signal parameters include, e.g., pulse shape, spectral profile of the signal, e.g., pulse spectral centroid, pulse height, pulse diffusion ratio, pulse spacing, total signal levels, and the like.

Either following or prior to identification of a significant signal pulse, signal data may be correlated to a particular signal type. In the context of the optical detection schemes used in conjunction with the invention, this typically denotes a particular spectral profile of the signal giving rise to the signal data. In particular, the optical detection systems used in conjunction with the methods and processes of the invention are generally configured to receive optical signals that have distinguishable spectral profiles, where each spectrally distinguishable signal profile may generally be correlated to a different reaction event. In the case of nucleic acid sequencing, for example, each spectrally distinguishable signal may be correlated or indicative of a specific nucleotide incorporated or present at a given position of a nucleic acid sequence. Consequently, the detection systems include optical trains that receive such signals and separate the signals based upon their spectra. The different signals are then directed to different detectors, to different locations on a single array based detector, or are differentially imaged upon the same imaging detector (See, e.g., U.S. Pat. No. 7,805,081, which is incorporated herein by reference in its entirety for all purposes).

In the case of systems that employ different detectors for different signal spectra, assignment of a signal type (for ease of discussion, referred to hereafter as "color classification" or "spectral classification") to a given signal is a matter of correlating the signal pulse with the detector from which the data derived. In particular, where each separated signal component is detected by a discrete detector, a signal's detection by that detector is indicative of the signal classifying as the requisite color.

In preferred aspects, however, the detection systems used in conjunction with the invention utilize an imaging detector upon which all or at least several of the different spectral components of the overall signal are imaged in a manner that allows distinction between different spectral components. Thus, multiple signal components are directed to the same overall detector, but may be incident upon wholly or partly different regions of the detector, e.g., imaged upon different sets of pixels in an imaging detector, and give rise to distinguishable spectral images (and associated image data). As used herein, spectra or spectral image generally indicates a pixel image or frame (optionally data reduced to one dimension) that has multiple intensities caused by the spectral spread of an optical signal received from a reaction location.

In its simplest form, it will be understood that assignment of color to a signal event incident upon a group of contiguous detection elements or pixels in the detector would be accomplished in a similar fashion as that set forth for separate detectors. In particular, the position of the group of pixels upon which the signal was imaged, and from which the signal data is derived, is indicative of the color of the signal component. In particularly preferred aspects, however, spatial separation of the signal components may not be perfect, such that signals of differing colors are imaged on overlapping sets of pixels. As such, signal identification will generally be based upon the aggregate identity of multiple pixels (or overall image of the signal component) upon which a signal was incident.

Once a particular signal is identified as a significant pulse and is assigned a particular spectrum, the spectrally assigned pulse may be further assessed to determine whether the pulse can be called an incorporation event and, as a result, call the base incorporated in the nascent strand, or its complement in the template sequence. Signals from the labeled leaving group (e.g., fluorophore labeled pyrophosphate; PPi+FL) are used to identify which base should be called. As set forth above, in one embodiment, by using the invention 3 enzyme polymerase-ATP Sulfurylase-Luciferase reaction system, a set of characteristic signals are produced which can be correlated with high confidence to an incorporation event.

In addition, calling of bases from color assigned pulse data will typically employ tests that again identify the confidence level with which a base is called. Typically, such tests will take into account the data environment in which a signal was received, including a number of the same data parameters used in identifying significant pulses. For example, such tests may include considerations of background signal levels, adjacent pulse signal parameters (spacing, intensity, duration, etc.), spectral image resolution, and a variety of other parameters. Such data may be used to assign a score to a given base call for a color assigned signal pulse, where such scores are correlative of a probability that the base called is incorrect, e.g., 1 in 100 (99% accurate), 1 in 1000 (99.9% accurate), 1 in 10,000 (99.99% accurate), 1 in 100,000 (99.999% accurate), or even greater. Similar to PHRED or similar type scoring for chromatographically derived sequence data, such scores may be used to provide an indication of accuracy for sequencing data and/or filter out sequence information of insufficient accuracy.

Once a base is called with sufficient accuracy, subsequent bases called in the same sequencing run, and in the same primer extension reaction, may then be appended to each previously called base to provide a sequence of bases in the overall sequence of the template or nascent strand. Iterative processing and further data processing can be used to fill in any blanks, correct any erroneously called bases, or the like for a given sequence.

Figure 13:
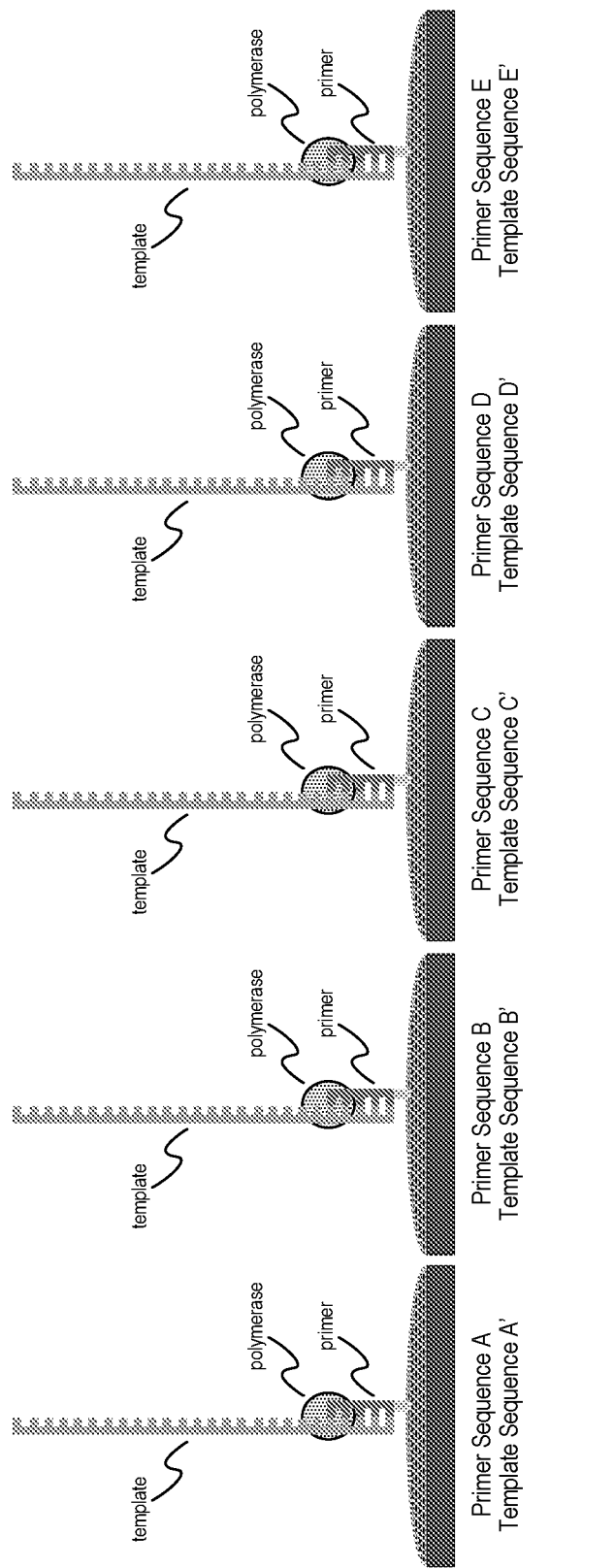
FIG. 13 shows an embodiment where numerous different (mutually exclusive) primers are bound to a substrate each at discreet loci, which can be in either a single overall reaction chamber, or in individual discreet reaction chambers. These primers bind different, mutually exclusive target template nucleic acids.

Analysis of sequencing-by-incorporation-reactions on an array of reaction locations according to specific embodiments of the invention can be conducted as illustrated graphically in FIG. 13 of U.S. Pat. No. 9,447,464, incorporated by reference in its entirety for all purposes). For example, data captured by a camera is represented as a movie, which is also a time sequence of spectra. Spectral calibration templates are used to extract traces from the spectra. Pulses identified in the traces are then used to return to the spectra data and from that data produce a temporally averaged pulse spectrum for each pulse, such pulse spectra will include spectra for events relating to enzyme conformational changes. The spectral calibration templates are then also used to classify pulse spectrum to a particular base. Base classifications and pulse and trace metrics are then stored or passed to other logic for further analysis. The downstream analysis will include using the information from enzyme conformational changes to assist in the determination of incorporation events for base calling. Further base calling and sequence determination methods for use in the invention can include those described in, for example, U.S. Pat. No. 8,182,993, which is incorporated herein by reference in its entirety for all purposes.

An advantage of the invention single molecule sequencing methods that permit the use of polymerase in an environment that is more optimized for polymerase, is the very low error rate achieved per sequencing run; or in other words the substantially high level of sequence accuracy obtained per sequencing run. For example, natural polymerase makes 1 error per 100 million bases; and this is contemplated herein as target error rate for the invention FLASH sequencing methods provided herein. Also in accordance with the present invention that uses a plurality of polymerases per target nucleic template, the error rate is independent of read length; therefore, the error rate can be improved by the selection of a higher fidelity polymerase and as a result require less coverage; and still can achieve very long read length by using a plurality of polymerases. Error rates achieved by polymerases used in the invention methods, per run before coverage is considered, are contemplated to be in the range selected from: 1%-30%, 1%-20%, 1%-10%, 1%-5%, 1%-3%, 1%-2%, 0.000001%-1%, 0.00001%-1%, 0.0001%-1%, 0.001%-1%, 0.01%-1%, 0.000001%-0.00001%, 0.000001%-0.0001%, 0.000001%-0.001%.

This advantage reduces the overall coverage required for obtaining an accurate sequence as defined by industry standards, which correspondingly reduces the overall cost of obtaining the nucleotide sequence. As used herein, coverage refers the number of sequencing runs required to obtain an accurate sequence for a particular target nucleic acid sequence within industry standards.

EXAMPLES

Example 1—Luminescence-Based Single Molecule Sequencing

Prior to undergoing a single molecule sequencing reaction, the respective fluorophores are attached to the terminal phosphate of its corresponding dNTP for each of dATP, dTTP, dGTP and dCTP. There is a different fluorophore for each dNTP base (A, T, G, C) (FIG. 1A). Since no fluorescence is produced at this time as there is no external light excitation, it not necessary to select a fluorophore that can be chemically quenched. During the single molecule sequencing reaction, upon interaction with the DNA polymerase, while the DNA polymerase binds the dNTP nucleotide analog to the complementary template strand, it cleaves off and releases a pyrophosphate that includes the additional fluorophore label attached thereto (PPi+FL) (FIGS. 1A and 1B). In this case there is no external light excitation and there is no need for dynamic, static or any other form of quenching mechanism of the labeled flourophore.

Once released, the labeled pyrophosphate (PP, +FL) interacts with ATP sulfurylase, which binds the labeled pyrophosphate to adenosine 5'-phosphosulfate (APS) yielding labeled-ATP, which still contains the fluorophore label (ATP+FL) (FIGS. 1B and 1C).

The labeled-ATP (ATP+FL) produced above is used to bind to Firefly luciferase that uses luciferin as a substrate (FIGS. 1D and 1E). With the labeled ATP (ATP+FL) acting as a cofactor, Firefly luciferase catalyzes luciferin (FIGS. 1D-1F). As a result of the enzymatic catalysis, luciferin is converted into oxyluciferin and luminescence is also produced for a discreet and limited time (FIG. 1F). As side products of the reaction, adenosine monophosphate and PPi+FL are generated. The fluorophore attached to the labeled pyrophosphate (PPi+FL) is excited by the luminescence produced for a limited period of time as a result of the luminescence reaction. This results in a detectable fluorescence emission during the discreet and limited period (lifetime) of the luminescence, which spectra of fluorescence light emission corresponds to the respective dNTP for the particular fluorophore (FIG. 1F). Accordingly, as a result of dNTP interacting with the DNA polymerase, fluorescence light is generated upon luminescence produced by the luminescence reaction produced by the luminescence-enzyme and luminescence-substrate, generating a fluorescence signal corresponding to the color of the fluorophore selected for the particular dNTP. Specificity of such interaction is further increased by the proximity of luminescence production and PPi+FL. The respective fluorescent light is the detected prior to the light vanishing after a discreet and limited period of time, such as in one embodiment, before the addition of the next dNTP.

This dNTP incorporation process is repeated until the desired nucleic acid read-length has been achieved.

Example 2—Parameters Affecting Luminescence Generation

Figure 2:
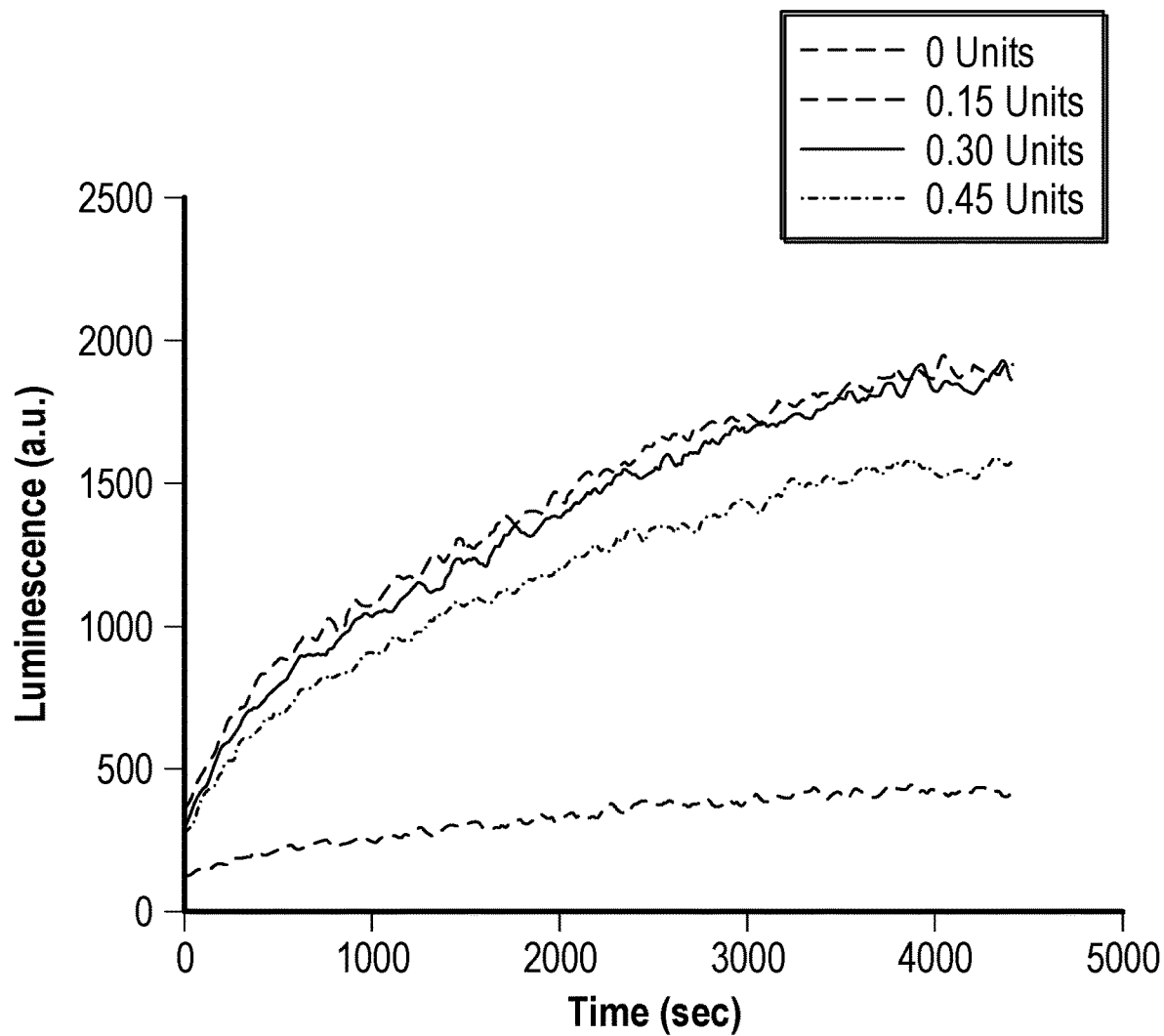
FIG. 2 shows Luminescence Generation as a Result of the invention FLASH Sequencing Reaction with Varying ATP Sulfurylase.
Figure 3:
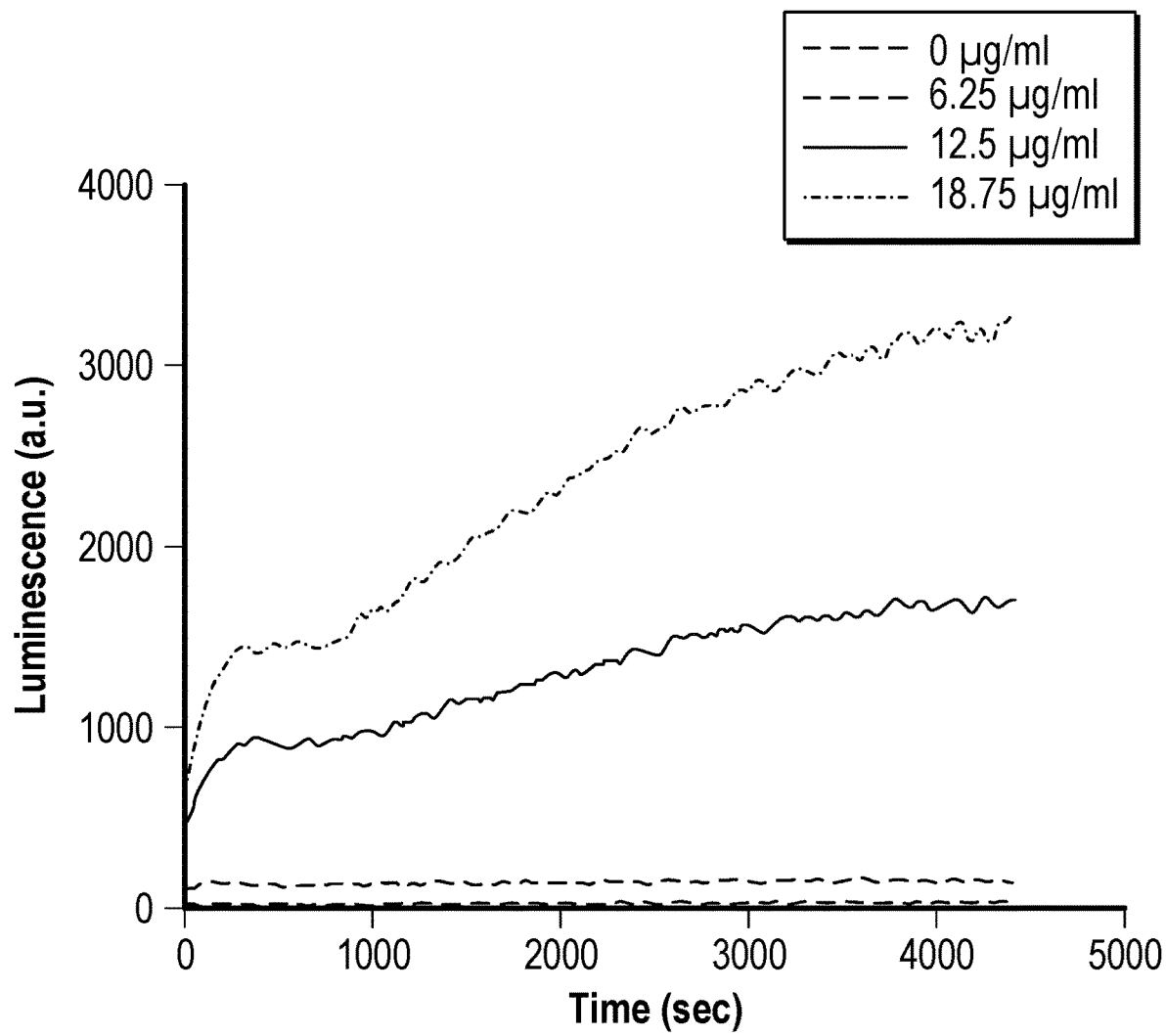
FIG. 3 shows Luminescence Generation as a Result of the invention FLASH Sequencing Reaction with Varying Firefly Luciferase.
Figure 4:
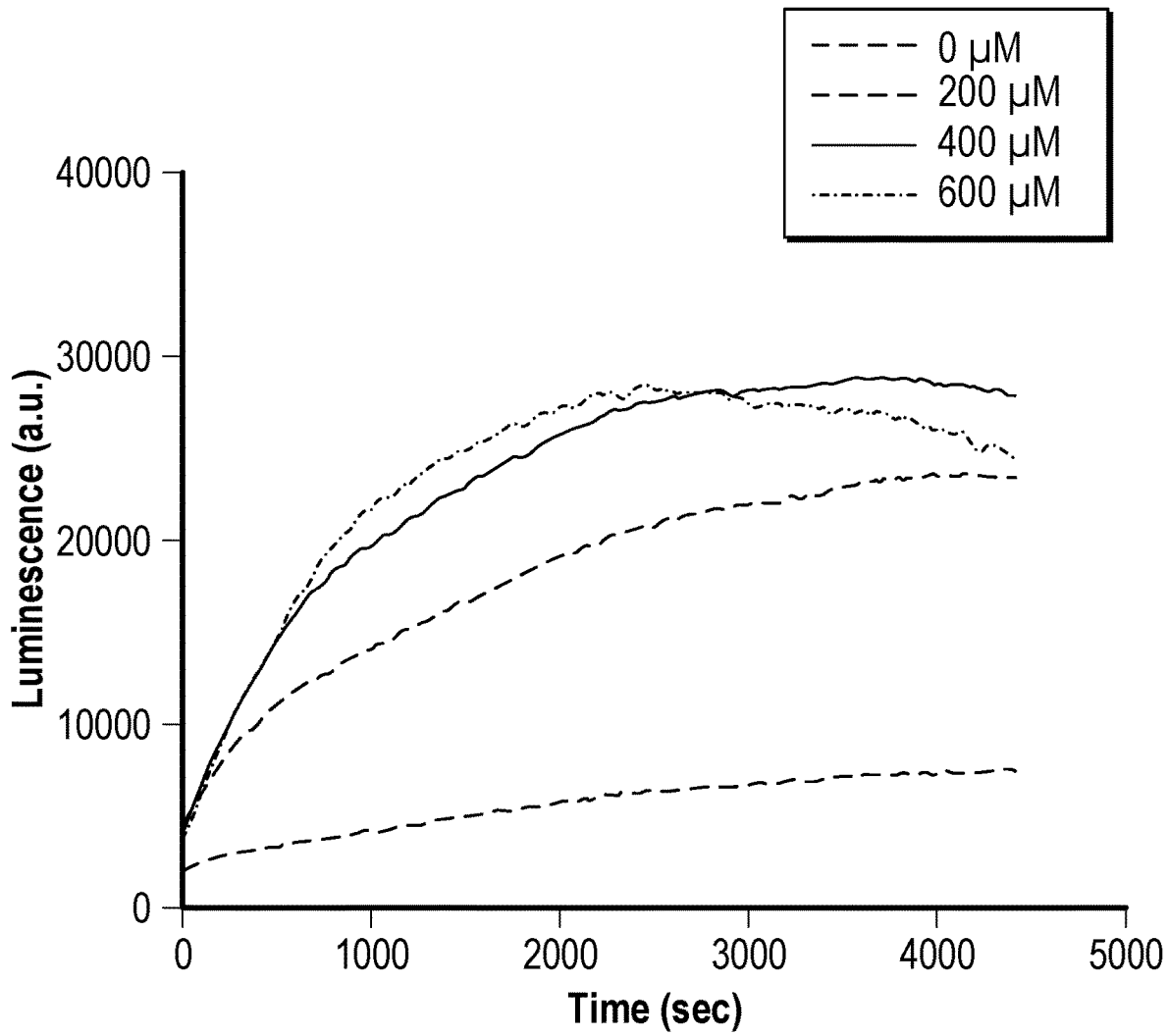
FIG. 4 shows Luminescence Generation as a Result of the invention FLASH Sequencing Reaction with Varying dGTP-Coumarin.

Example 2A—Effects of Varying the Respective Concentrations of ATP Sulfurylase, Firefly Luciferase, and the Luminescence-Substrate—dGTP-Coumarin In this reaction, a 300 bp single-stranded DNA template was produced made up of all cytosine bases except for the start sequence of a 20 bp region formed by a mixture of 4 bases (dATP, dGTP, dTTP, dCTP). In addition to the template DNA, the reaction contained primer oligonucleotides complementary to the start sequence, dGTP-Coumarin, ATP Sulfurylase, Adenosine 5'-phosphosulfate, Firefly luciferase (as the luminescence-enzyme), and luciferin (as the luminescence-substrate). The effects of varying the respective concentrations of ATP Sulfurylase, Firefly luciferase, and the luminescence-substrate, dGTP-Coumarin are shown in FIGS. 2-4, respectively. As can be seen in FIGS. 2-4, starting with dGTP-Coumarin (which is a dGTP labeled by Coumarin at the terminal phosphate), this concatenated three-enzyme system of Polymerase-ATP Sulfurylase-Firefly luciferase utilized herein (also designated the FLASH approach) was surprisingly found to generate luminescence in a final step. In this particular case, as the excitation spectra of Coumarin peaks at 385 nm while the emission spectra peaks at 502 nm, the luminescence produced by this reaction (peaks at 560 nm) cannot be used to observe fluorescence emission from Coumarin as a result.

However, in other embodiments, it is contemplated herein that fluorophore labels having an excitation spectra near 560 nm, such as DDAO ([7-hydroxy-9H-(1,3-dichloro-9,9-dimethylacridin-2-one)]), and the like, will produce a detectable light fluorescence emission corresponding to its respective dNTP. For example, the following labelled dNTPs were synthesized and obtained from Jena Bioscience (Jena, Germany) for use herein with the invention methods:

gamma-(6-Aminohexyl)-2'-deoxyadenosine-5'-triphosphate, labeled with ATTO680, Triethylammonium;
gamma-(6-Aminohexyl)-2'-deoxycytidine-5'-triphosphate, labeled with ATTO680, Triethylammonium salt;
gamma-(6-Aminohexyl)-2'-deoxythymidine-5'-triphosphate, labeled with ATTO680, Triethylammonium salt;
gamma-[(6-Aminohexyl)imido]-dGTP-ATTO-647N;
gamma-[(6-Aminohexyl)imido]-dGTP—Cy5;
gamma-(6-Aminohexyl)-dGTP—Cy5;
gamma-(6-Aminohexyl)-2'-deoxythymidine-5'-triphosphate, labeled with Alexa700, Triethylammonium salt;
gamma-(6-Aminohexyl)-2'-deoxyadenosine-5'-triphosphate, labeled with Alexa660, Triethylammonium salt; and
gamma-(6-Aminohexyl)-2'-deoxythymidine-5'-triphosphate, labeled with ATTO700, Triethylammonium salt.

Example 2B—Effects of Adding ATP Sulfurylase and APS to a Luciferase Reaction

The following reagents of the sequence mixture were used in this experiment:

| | | |
|---|---|---|
| 10x TAE Buffer 17.5 uL | | |
| Luciferase (5 mg/ml in 1M Tris) (1:50) 17.5 uL | 250 ng | Sigma |
| Cyc-Luc(10 mg/mL) (1:10 in 1xTAE) 35 uL | 5 ug | EMD Millipore |
| ATP (100 mM) (1:5k) 35 uL | 1.2 uM | Sigma |
| CoA (10 mM) (1:20) 35 uL | 2 mM | Sigma |
| MgCl2 (10 mM) = (2.5 uL per rxn) | 1 mM | NEB |
| PPase 1x(=no dil) (200 U/mL) = 0.5 uL | 0.1 U | Sigma |
| ASulf (300 U/mL) = 0.5 uL | 0.15 U | NEB |
| APS (10 mM) = 1 uL | 377 uM | Sigma |

In order to study the effect of the ATP sulfurylase/luciferase signal amplification loop on the fluorescent signal level, one can observe the ATPSulfurylase-Luciferase couple alone. The reactions were performed in 1×TAE Buffer with 750 ng of Luciferase, 5 μg of Cyc-Luc luciferin, 1.2 μM of ATP, 2 mM of Coenzyme A, 1 mM MgCl2 0.15 units of ATP Sulfurylase, 377 μM of APS. The variation of pyrophosphatase corresponds to 0.1, 0.005 and 0.002 unit amounts. The Luciferase, ATP, Coenzyme A, Pyrophosphatase and APS were obtained from Sigma. The ATP Sulfurylase and MgCl2 were obtained from NEB.

Initially Pyrophosphatase and MgCl2 were dispensed into the relevant wells in a 384-well microplate. Then a mastermix of buffer, Luciferase and Coenzyme A was prepared, mixed and dispensed into the relevant wells in equal amounts. Then Cyc-Luc luciferin was added to each well and finally ATP was added to each well. The plate was then shaken for 15 seconds before measurements were taken from a FLUOstar Optima plate reader.

Figure 7:
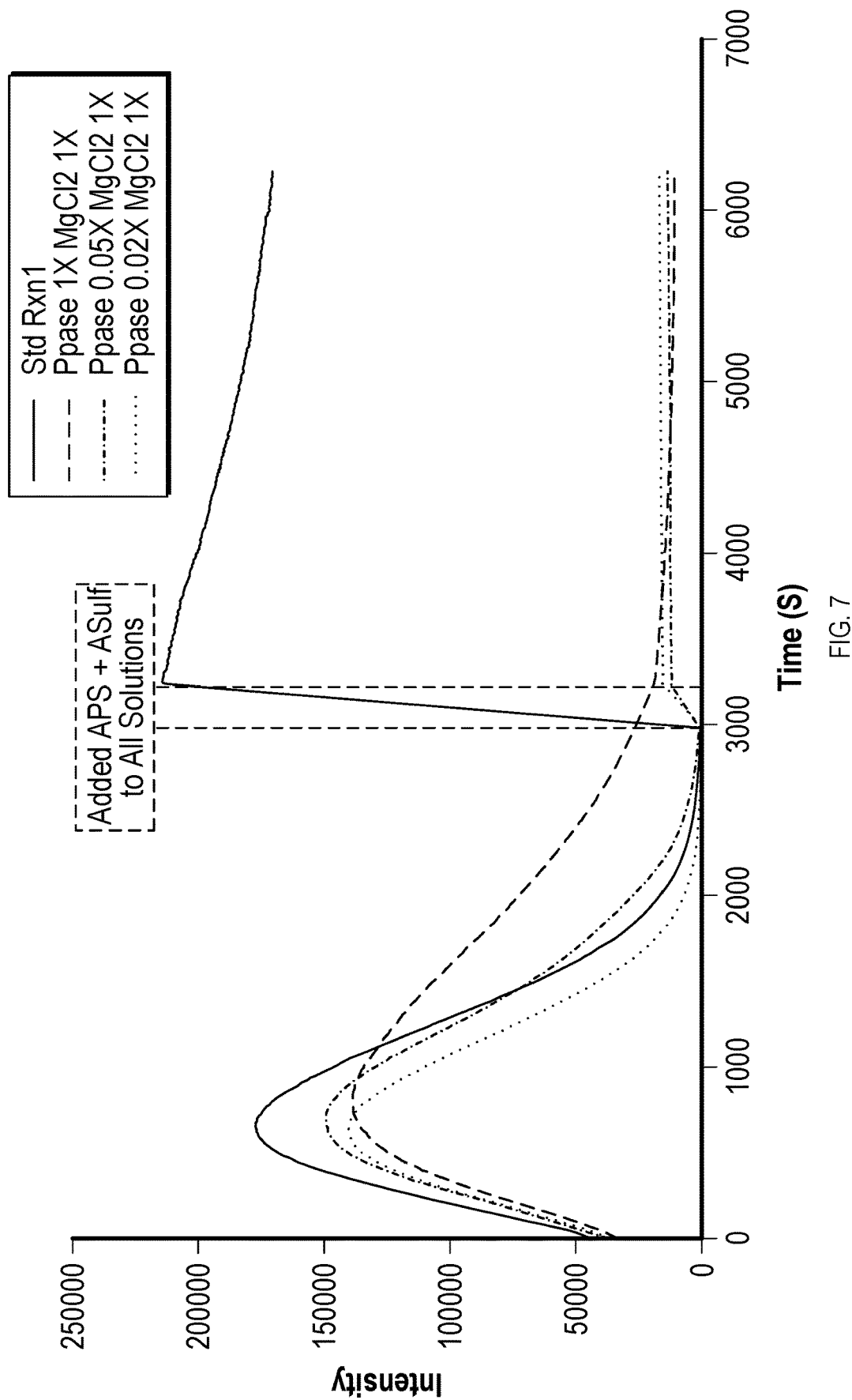
FIG. 7 shows the results of adding ATP and APS to a Luciferase reaction with varying amounts of inorganic phosphatase.

In this example, a standard reaction corresponding to a luciferase reaction alone using and luciferin as substrates is shown as the solid line plot in FIG. 7. In FIG. 7, the solid line plot shows a rise and decay of luminescense signal as expected from a regular luciferase reaction. At time 3000 s, ATP-Sulfurylase and APS was added to the standard reaction, which as can be seen in FIG. 7, started the ATP Sulfurylase/Luciferase Signal Amplification Loop and caused amplification of the signal (see FIG. 7, solid line plot starting at 3000s). These results indicate that the luminescence signal (and therefore the subsequent fluorescence signal) generated by the invention sequencing methods can be amplified by the addition of an ATP regenerating enzyme (ATP Sulfurylase in this example) and its cognate ATP regenerating enzyme substrate (APS in this example), which initiates an ATP Sulfurylase/Luciferase Signal Amplification Loop.

Three other reactions similar to the standard reaction were carried out, where varying relative dilutions of inorganic pyrophosphate were added in the amounts of 0.02× (1:50 dilution), 0.05× (1:20 dilution) and 1× (no dilution) of pyrophosphatase 1×, along with 1× of MgCl2. As seen in FIG. 7, the loop signal is diminished with addition of inorganic pyrophosphatase (0.02× Ppase dotted plot and 0.05× Ppase dashed plot). In higher concentrations of inorganic pyrophosphatase, the loop is completely diminished (1× Ppase dashed plot). This indicates that the level of luminescence signal amplified by the ATP Sulfurylase/Luciferase Signal Amplification Loop can be advantageously controlled by adjusting the concentration ratio of pyrophosphatase relative to the concentration of ATP sulfurylase.

Example 2C—Effect of Adding Coenzyme a to the ATP Sulfurylase/Luciferase Signal Amplification Loop Reaction on Luminescence Signal The effect of adding Coenzyme A to the ATP sulfurylase/luciferase signal amplification loop on the luminescent signal level was studied by running a standard luciferase reaction as in Example 2B. The reactions were performed in 1×TAE Buffer with 750 ng of Luciferase, 5 µg of Cyc-Luc luciferin, 1.2 µM of ATP, 2 mM of Coenzyme A, 1 mM MgCl2 0.15 units of ATP Sulfurylase, 200 µM of APS. The Luciferase, ATP, Coenzyme A, and APS were obtained from Sigma. The ATP Sulfurylase and MgCl2 were obtained from NEB. Initially ATP Sulfurylase, APS, Coenzyme A and MgCl2 were dispensed into the relevant wells in a 384-well microplate. Then a mastermix of buffer, Luciferase and Cyc-Luc luciferin was prepared, mixed and dispensed into the relevant wells in equal amounts. Then ATP was added to each well. The plate was then shaken for 15 seconds before measurements were taken from a FLUOstar Optima plate reader.

Figure 8:
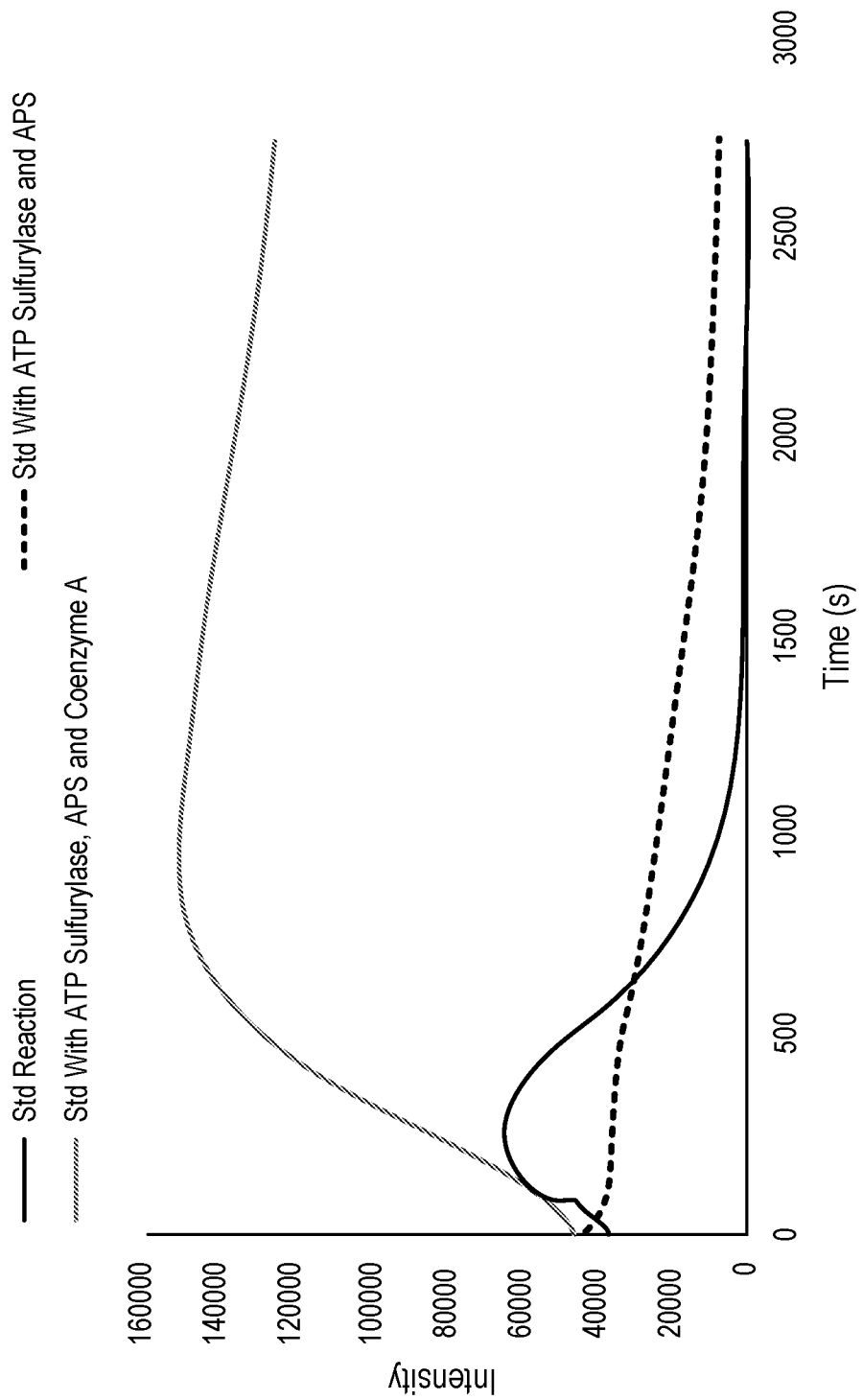
FIG. 8 shows the effect of Adding Coenzyme A to the ATP Sulfurylase/Luciferase Signal Amplification Loop Reaction on Luminescence Signal.

The results of the luminescence emission of standard luciferase reaction, which contains Luciferase, Luciferin and ATP, are shown in the dark solid line plot of FIG. 8. In FIG. 8, the dark solid line plot shows a rise and decay of luminescent signal as expected from a regular luciferase reaction. The dashed line plot show the luciferase reaction with ATP Sulfurylase and APS. The light line plot of FIG. 8 shows the case for the luciferase-ATP Sulfurylase concatenate together with APS and Coenzyme A. In this example of APS and Coenzyme co-administration, the fluorescent signal level is much higher and signal is more durable. These results indicate that Coenzyme A, has a positive effect on the signal, which is believed to occur by preventing damage to the luciferase and stabilizing the luciferase/luciferin couple thereby improving the loop efficiency.

Example 3—Adjusting Eznyme Ratios to Break the Enzymatic Loop

Following luminescent reaction catalyzed by luciferase a new pyrophosphate molecule is released still having the fluorescent label attached (PPi+FL) (FIG. 1.F). This newly released PPi-FL can once again be a substrate for ATP Sulfurylase thereby generating an enzymatic loop between ATP sulfurylase and luciferase (FIG. 1.G.Top). With this loop PPi+FL is recycled by ATP Sulfurylase and converted into fluorescently labeled ATP (ATP-FL), which can then be catalyzed by luciferase releasing PPi-FL. This will generate successive signals from the labeled pyrophosphate, and thereby serve as an amplification mechanism for the sequencing signal for the most recent nucleotide. However, during this loop, if the polymerase undergoes another nucleotide incorporation to the template, the continuing PPi-FL loop might result in error in the reading.

To break this reaction loop, pyrophosphatase enzyme is introduced into the reaction (FIG. 1G.Bottom). Pyrophosphatase catalyzes hydrolysis of pyrophosphate into two phosphate ions breaking the loop. However, pyrophosphatase might also use the initial pyrophosphate released right after nucleotide incorporation by polymerase. This could result in loss of the signal produced as a result of incorporation.

To reduce the signal loss and also benefit from the amplification effect of the loop there are multiple approaches to control pyrophosphatase activity:

First, the ratios of enzyme concentration are adjusted in a way that ATP sulfurylase activity is orders of magnitude higher than the pyrophosphatase activity. This makes the initial interaction of pyrophosphatase with the pyrophosphate produced by polymerase reaction very unlikely and also will allow the loop to run numerous times to achieve the amplification effect. However, eventually, there will be some interaction with pyrophosphate, which will stop the loop or might result in a read error. If the ratio of pyrophosphatase and ATP sulfurylase is adjusted accordingly, this error is very rare while allowing some amplification effect before stopping the loop. The loop continues for a large number of times before the incorporation of new nucleotide since the polymerase incorporation is orders of magnitude slower than both pyrophosphatase and ATP Sulfurylase activity.

The reaction rate of polymerase, the ATP-Sulfurylase/Luciferase loop as well as the hydrolysis of pyrophosphate can each be adjusted independently from each other. Here, the goal is to maximize the number of times the ATP-Sulfurylase/Luciferase loop occurrs before pyrophosphate is hydrolysed by pyrophosphatase; and making sure the loop ended before polymerase goes into another incorporation event. Another consideration is that pyrophosphate's interaction must be more likely with ATP Sulfurylase compared to pyrophoshatase, otherwise there would be a reading error if a pyrophosphate is hydrolyzed right after it is released by polymerase.

As the reaction rate of polymerase is dramatically slow compared to other enzymes in the reaction with typically around 1000 nucleotides per second (or slower)(Fijalkowska, et al., FEMS Microbiol. Rev. 36, 1105-1121 (2012); and Lapenta, F. et al. PLOS ONE 11, e0152915 (2016)); and as a nucleotide incorporation event is required for the production of pyrophosphate, it is contemplated herein to adjust the relative reaction rate of ATP-Sulfurylase/ Luciferase loop to be in the range of about $10^2$-$10^9$ times faster than pyrophosphate, ensuring an error rate of 10-10$^{-4}$% per nucleotide statistically. In other embodiments, it is also contemplated herein to adjust the relative reaction rate of ATP-Sulfurylase/Luciferase loop to be about $10^3$-$10^9$ times faster than pyrophosphate. In other embodiments, it is also contemplated herein to adjust the relative reaction rate of ATP-Sulfurylase/Luciferase loop to be about $10^3$, $10^4$, $10^5$, $10^6$, $10^7$, $10^8$, and $10^9$ times faster than pyrophosphate. Considering the typical error rates of prior art sequencing technologies being >15% per run (Goodwin, et al., Nat. Rev. Genet. 17, 333-351 (2016)), the invention methods provide a significant improvement over conventional approaches. This configuration can also be adjusted in a way that the slowest reaction, pyrophosphate hydrolysis, is still much faster than polymerase so that pyrophosphate hydrolysis occurs after going through the ATP-Sulfurylase/Luciferase loop many times before another nucleotide incorporation event occurs.

Example 4—Co-Encapsulation of Luciferase & Pyrophosphatase to Avoid the Enzymatic Loop As another way to avoid the enzymatic reaction loop between ATP sulfurylase and luciferase (FIG. 1G-Top), co-encapsulation of luciferase and pyrophosphatase in an ideally negatively charged nano/micro matrix (FIG. 5) is used. This matrix can be in the form of a nanoparticle with a high encapsulation of luciferase and pyrophosphatase. The ATP molecule essentially does not express a net charge while PPi-FL expresses a net negative charge. After PPi-FL is released following the incorporation reaction by polymerase, PPi-FL has a higher chance of interacting with ATP sulfurylase rather than the pyrophosphate, which is encapsulated within the negatively charged matrix as the charge of the matrix will repel PPi-FL. ATP Sulfurylase releases labeled ATP (ATP-FL). Since ATP-FL does not express a negative charge, it is able to diffuse into the negatively charged matrix in which luciferase and pyrophosphatase is encapsulated. Then, ATP-FL interacts with luciferase. When PPi-FL is released it first encounters pyrophosphatase that will convert PPi-FL into phosphate ion within the matrix eliminating the fluorescent label to be recycled into any other reaction in the system.

In particular embodiments, the luciferase and pryophosphatase enzymes can be linked or tethered to each other using methods well known in the art, such as by crosslinking described in U.S. Pat. No. 4,975,278, which is incorporated herein by reference in its entirety.

Example 5—Labelled Enzymatic Concatenate Functioning with Labeled Substrates Produces Both Luminescence and Fluorescence In contrast to prior art pyrosequencing methods, the invention FLASH sequencing method uses gamma phosphate labeled nucleotides combined with a similar three enzyme concatenate used in pyrosequencing in order to achieve real-time single molecule sequencing. In the invention FLASH method, each enzyme involved in the reaction catalyzes conversion of the labeled substrates. In the first reaction, polymerase attaches gamma phosphate labeled dNTP, which results in cleaving the labeled pyrophosphate (see FIGS. 1A and 1B). Next, labeled ATP Sulfurylase generates labelled ATP using labeled pyrophosphate and APS (FIG. 1C), where the generated ATP still carries the original label in the gamma phosphate. Then, that labeled ATP is further used by luciferase releasing labeled pyrophosphate and generating luminescence (FIGS. 1D-1F). Failure of any of the steps prior to luminescence generation might prevent readout, whereas luminescence generation is a confirmation of successful completion of these prior steps.

The following reagents of the sequence mixture were used in this experiment:

| | | |
|---|---|---|
| 10x TAE 2.5 uL | | |
| Luciferase (5 mg/ml in 1M Tris) 0.25 uL | 1.25 ug | Sigma |
| Cyc-Luc (10 mg/mL) (1:10 in dMSO) 2.5 uL | 2.5 ug | EMD Millipore |
| Sequenase Buffer (10X) 2.5 uL | | Thermofisher |
| Sequenase (13 U/uL) = 0.25 uL | (3.25 Units) | Thermofisher |
| Template 500 nM = 0.5 uL | 10 nM | IDT |
| Primer 100 uM = 0.5 uL | 2 uM | IDT |
| dGTP, Cy5, Atto647 1 mM = 5 uL | 200 uM | Jena Bioscience |
| MgSO4 (100 mM) = (1.25 uL per rxn) | 1 mM | NEB |
| ASulf (300 U/mL) = 0.25 uL | 0.075 U | NEB |
| APS (10 mM) = 0.5 uL | 200 uM | Sigma |

In this example, the invention FLASH sequencing reaction set forth herein was conducted. The reactions were performed in 1×TAE Buffer and 10× Sequenase Buffer with 1.25 μg of Luciferase, 2.5 ng of Cyc-Luc luciferin, 325 units of Sequenase, 10 nM Cytosine-homopolymer, 2 μM primer, 200 μM dGTP, 200 μM dGTP-Cy5, 200 μM dGTP-ATTO-647, 1 mM MgSO4, 0.075 units of ATP Sulfurylase, 200 μM of APS. The Luciferase, and APS were obtained from Sigma. The ATP Sulfurylase and MgSO4 were obtained from NEB. The Sequenase and sequenase buffer were obtained from Thermofisher. The Cytosine-homopolymer and primer were obtained from IDT. The dGTP-ATTO647 was obtained from Jena Biosciences.

Initially two separate master mixes were prepared. The first master mix contained water, Sequenase reaction buffer, Sequenase, the Cytosine-homopolymer, the primer, APS and ATP Sulfurylase. The second master mix contained water 1×TAE buffer, MgSO4, luciferase and Cyc-Luc luciferin. Each of the master mixes were mixed and aliquots of each master mix were taken and combined, at which point the dNTPs were added to prepare the FLASH reaction. This reaction was placed into a well on a 384-well microplate which was then placed into a customized optical setup with lenses to focus the light output and a PMT photodetector to detect the light. Each filter was manually changed to obtain the spectra of each FLASH reaction mix.

Figure 6:
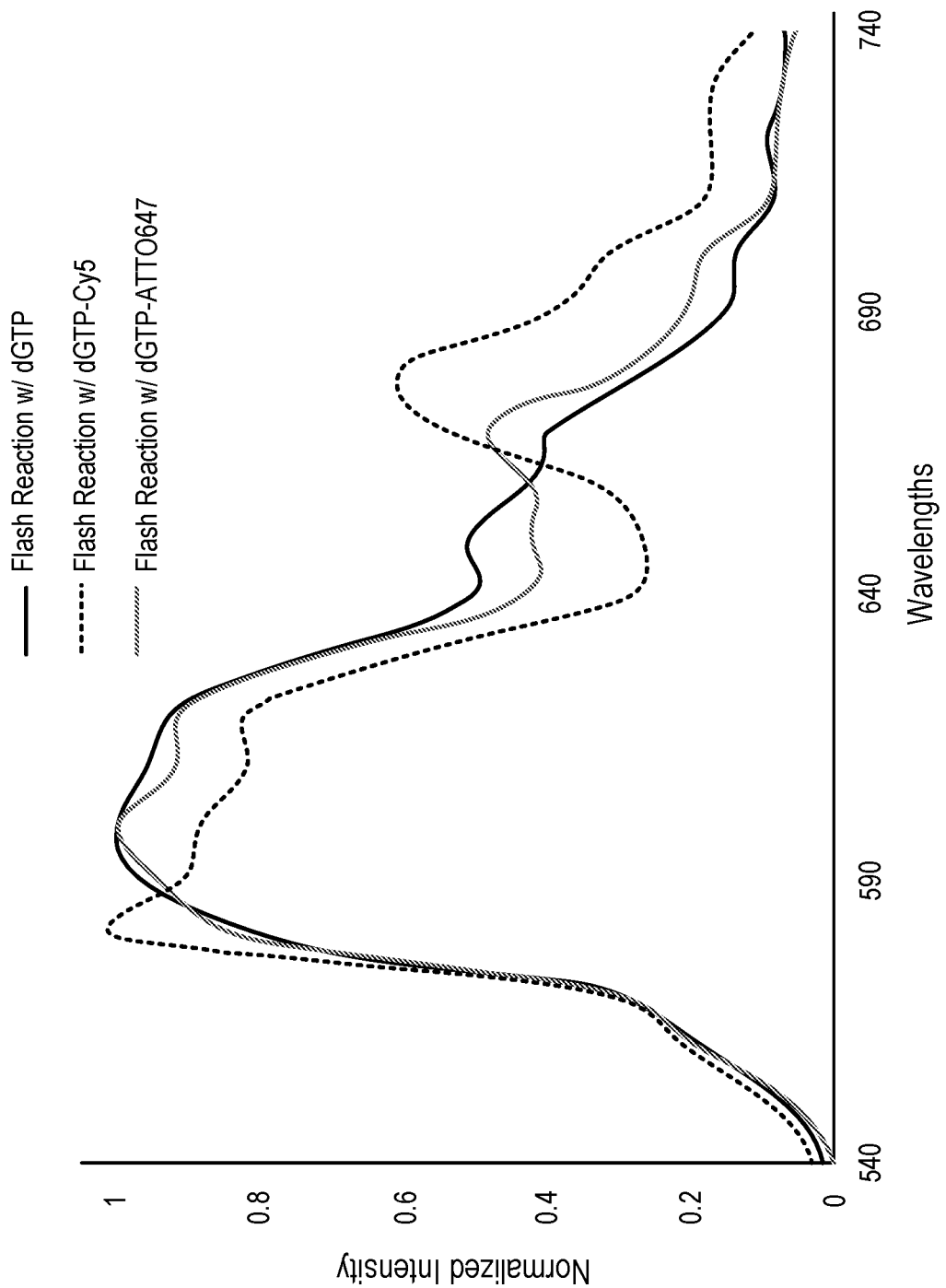
FIG. 6 shows the results of carrying out the invention FLASH sequencing reaction fluorescently labeled and unlabeled dGTP.

In this example, the invention FLASH sequencing reaction set forth herein was conducted, where the sequencing mixture included a polymerase-ATPSulfurylase-Luciferase concatenate and the target template nucleic was a Cytosine-homopolymer* (SEQ ID NO:1). In this case, since there is no external excitation source, the spectrum is the light emission spectrum without external amplification. The results show the generation of luminescence, where luminescence can only be generated if all the reactions are completed. Therefore, the results indicate that all reactions of the sequencing method were completed. As seen from the spectrum shown in FIG. 6, when unlabeled dGTP was added into the solution, luminescence was generated demonstrating successful operation of enzyme concatenate described (FIG. 6; dark solid plot). When gamma-phosphate-labeled-dGTP was used instead of unlabeled dGTP, again, the luminescence signal was observed demonstrating completion of all reactions. However, for these 2 gamma-phosphate-labeled-dGTP, an extra fluorescence emission peak was also surprisingly observed at around 670 nm corresponding to the fluorescence emission peak of dGTP-ATTO647 (FIG. 6; light solid plot); and around 680 nm corresponding to the fluorescence emission peak of dGTP-Cy5 (FIG. 6; dashed plot). In this particular case, the fluorescent label is Cy5. This confirms that when the substrates are labelled, this enzymatic concatenate still functions with labelled substrates leading to luminescence. In addition, it was shown that the luminescence generated from the luciferase reaction was used to excite the labelled pyrophosphate produced by that luciferase luminescence reaction (FIGS. 1E-1F). Thus, another key event in the process has been demonstrated; corresponding to the excitation of the fluorescent label in pyrophosphate that was released by luciferase, where this excitation was caused by the luminescence generated by the luciferase reaction shown in FIGS. 1D-1F. These results show that the catalysis of luciferin using labeled ATP and luciferase results in emission of fluorescent light that is specific for each respective labelled dNTP.

\* Template DNA
(SEQ ID NO: 1)
(5'-CCC CCC CCC CCC CCC CCC CCC CCC CCC CCC CCC CCC CCC CCC CCC CCC CCC CCC CCC CCC CCC CCC CCC AAA TCT TAT CAT CGG TCG GTG-3')

Primer
(SEQ ID NO: 2)
(5'-CAC CGA CCG ATG ATA AGA TTT G-3')

While the present embodiments have been particularly shown and described with reference to example embodiments herein, it will be understood by those of ordinary skill in the art that various changes in form and details may be made therein without departing from the spirit and scope of the present embodiments as defined by the following claims. Those skilled in the art will recognize, or be able to ascertain using no more than routine experimentation, numerous equivalents to the specific procedures described herein. Such equivalents are considered to be within the scope of the present invention and are covered by the following claims. The contents of all non-patent literature publications, patents, and patent applications cited throughout this application are hereby incorporated by reference in their entirety for all purposes. The appropriate components, processes, and methods of those patents, applications and other documents may be selected for the present invention and embodiments thereof.

SEQUENCE LISTING

The sequence listing submitted herewith in the ASCII text file entitled "Innovasion_002WO1_ST25_Sequence_Listing_124667-002WO1.TXT," created Apr. 15, 2019, with a file size of 725 bytes, is incorporated herein by reference in its entirety.

What is claimed is:

1. A method for sequencing a nucleic acid template comprising:
providing a sequencing mixture comprising (i) a polymerase enzyme, (ii) an ATP regenerating enzyme, (iii) a luminescence enzyme, (iv) a template nucleic acid, and (iii) a polymerase-ATP regenerating enzyme-luminescence reagent solution having the components for carrying out template directed synthesis of a growing nucleic acid strand, wherein said reagent solution includes an ATP-regenerating-enzyme-substrate, a luminescence-substrate; and a plurality of types of nucleotide analogs; wherein each type of nucleotide analog has a labeled leaving group that is cleavable by the polymerase, and each type of nucleotide analog has a different label, wherein the labeled leaving group is cleaved upon polymerase-dependent binding of a respective nucleotide analog to the template strand;
carrying out nucleic acid synthesis such that a plurality of nucleotide analogs are added sequentially to the template whereby: a) a nucleotide analog associates with the polymerase, b) the nucleotide analog is incorporated on the template strand by the polymerase when the labeled leaving group on that nucleotide analog is cleaved by the polymerase, wherein the labeled leaving group is combined with an ATP-regenerating-enzyme-substrate by the ATP regenerating enzyme yielding labeled-ATP, then c) binding the labeled-ATP to a luminescence-enzyme, wherein a luminescence-substrate is catalyzed by the luminescence-enzyme to produce luminescence for a limited period of time and regenerate the respective labeled leaving group, wherein said luminescence causes the label on the respective labeled leaving group to produce light; and
detecting light from the labels while nucleic acid synthesis is occurring, and using light detected during each discreet luminescence period, to determine a sequence of the template nucleic acid, wherein the luminescence-enzyme is a luciferase, and wherein the luciferase and pyrophosphatase are co-encapsulated in a nanomatrix.

2. The method of claim 1, wherein the nucleotide analog has been modified by a fluorophore attached to a terminal phosphate.

3. The method of claim 1, wherein the leaving group is a labelled pyrophosphate.

4. The method of claim 3, wherein the pyrophosphate is labeled with a fluorophore.

5. The method of claim 1, wherein each base of a nucleotide is labeled with a unique fluorophore relative to other bases.

6. The method of claim 1, wherein the luciferase is firefly luciferase.

7. The method of claim 1, wherein the luminescence-substrate is luciferin.

8. The method of claim 1, wherein the polymerase enzyme is DNA polymerase.

9. The method of claim 1, wherein the ATP regenerating enzyme is selected from ATP Sulfurylase, AGPPase, and PPDK.

10. The method of claim 1, wherein the ATP-regenerating-enzyme-substrate is selected from APS, ADP-glucose, and AMP+PEP.

11. The method of claim 1, wherein the labeled leaving group is combined with APS by ATP Sulfurylase; with ADP-glucose by AGPPase; or with AMP+PEP by PPDK.

12. The method of claim 1, wherein types of nucleotide analogs comprise dATP, dTTP, dGTP, dCTP, dUTP, dGTPaS, dCTPaS, dTTPaS and dATPaS.

13. The method of claim 1, wherein the sequencing mixture further comprises a pyrophosphatase enzyme capable of converting the labeled pyrophosphate into 2 phosphate ions.

14. The method of claim 13, wherein the ratios of enzyme concentrations are adjusted such that ATP sulfurylase/Luciferase loop activity is orders of magnitude higher than the pyrophosphatase activity.

15. The method of claim 14, wherein the relative reaction rate of ATP-Sulfurylase/Luciferase loop is selected from the group consisting of at least: to 102, 103, 104, 105, 106, 107, 108, 109, 1010, 1011, 1012 times faster than the pyrophosphatase reaction.

16. The method of claim 1, wherein the nanomatrix is a nanoparticle that is negatively charged.

17. The method of claim 16, wherein labeled ATP (ATP-FL) is able to diffuse into the negatively charged nanomatrix in which luciferase and pyrophosphatase are co-encapsulated.

18. The method of claim 1, wherein the step c) binding the labeled-ATP to a luminescence-enzyme, wherein a luminescence-substrate is catalyzed by the luminescence-enzyme, occurs within the nanomatrix.

19. The method of claim 1, wherein a plurality of polymerase enzymes are used.

20. The method of claim 1, wherein a plurality of polymerase enzymes are use in a ratio of polymerase to template is selected from the group consisting of at least 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 150:1, 200:1, 250:1, 300:1, 350:1, 400:1, 450:1, 500:1, 550:1, 600:1, 650:1, 700:1, 750:1, 800:1, 850:1, 900:1, 950:1, 1000:1, 10000:1, 20000:1, 30000:1, 40000:1, 50000:1, 60000:1, 70000:1, 80000:1, 90000:1, 100000:1, 200000:1, 300000:1, 400000:1, 500000:1, 600000:1, 700000:1, 800000:1, 900000:1, and at least 1000000:1.

* * * * *